(12) United States Patent
McGraw et al.

(10) Patent No.: US 10,927,398 B2
(45) Date of Patent: Feb. 23, 2021

(54) COMPOSITIONS FOR CYP450 PHENOTYPING USING SALIVA SAMPLES

(71) Applicant: Concordia University, Inc., Mequon, WI (US)

(72) Inventors: Joseph McGraw, Germantown, WI (US); Armin Gerhardt, Mettawa, IL (US)

(73) Assignee: Concordia University Inc., Mequon, WI (US)

( * ) Notice: Subject to any disclaimer, the term of this patent is extended or adjusted under 35 U.S.C. 154(b) by 73 days.

(21) Appl. No.: 15/779,788

(22) PCT Filed: Nov. 30, 2016

(86) PCT No.: PCT/US2016/064210
§ 371 (c)(1),
(2) Date: May 29, 2018

(87) PCT Pub. No.: WO2017/095921
PCT Pub. Date: Jun. 8, 2017

(65) Prior Publication Data
US 2019/0264252 A1    Aug. 29, 2019

Related U.S. Application Data

(60) Provisional application No. 62/386,389, filed on Nov. 30, 2015.

(51) Int. Cl.
| | |
|---|---|
| *C12Q 1/26* | (2006.01) |
| *G01N 33/74* | (2006.01) |
| *A61K 9/46* | (2006.01) |
| *A61K 9/20* | (2006.01) |
| *A61K 9/00* | (2006.01) |

(52) U.S. Cl.
CPC .............. *C12Q 1/26* (2013.01); *G01N 33/743* (2013.01); *A61K 9/0007* (2013.01); *A61K 9/0056* (2013.01); *A61K 9/2054* (2013.01); *G01N 2333/90241* (2013.01)

(58) Field of Classification Search
CPC combination set(s) only.
See application file for complete search history.

(56) References Cited

U.S. PATENT DOCUMENTS

2005/0233470 A1    10/2005   Clark

FOREIGN PATENT DOCUMENTS

| WO | 2006112513 A1 | 10/2006 |
|---|---|---|
| WO | 2017095921 A1 | 6/2017 |

OTHER PUBLICATIONS

Jurica, J. et al., Topics on Drug Metabolism, 2012 pp. 191-220.*
Jurica, J. et al., "Metabolic Activity Using Selective Markers," ch 8 in Topics on Drug Metabolism, Paxton, J., ed. 2012, InTechOpen ISBN-10 9535100998.*
International Search Report and Written Opinion for PCT/US2018/045618 dated Nov. 22, 2018.
Cook CS., et al., Involvement of CYP3A in the metabolism of eplerenone in humans and dogs: differential metabolis by CYP3A4 and CYP3A5, Drug Metab Dispos. Dec. 2002; 30(12): 1344-51.
Cook CS. et al., Pharmacokinetics and metabolism of [14C]eplerenone after oral administration to humans. Drug Metab. Dispos. Nov. 2003; 31( I I ): 1448-55.
Isoherranen N. et al., The influence of CYP3A5 expression on the extent of hepatic CYP3A inhibition is substrate-dependent: an in vitro-in vivo evaluation, Drug Metab Dispos. Jan. 2008;36(1):146-54.
European Patent Office, Extended European Search Report for application 16871419, dated Jul. 3, 2019.
Streetman D: "Combined phenotypic assessment of CYP1A2, CYP2CI9, CYP2D6, CYP3A, N-acetyltransferase-2, and xanthine oxidase with the "Cooperstown cocktail"", Clinical Pharmacology and Therapeutics, vol. 68, No. 4, Oct. 1, 2000.
Shelepova T et al: "Effect of oral contraceptives (OCs) on drug metabolizing enzymes (DMES) as measured by the validated cooperstown 5+1 cocktail (5+1)", Clinical Pharmacology and Therapeutics, Nature Publishing Group, US, vol. 73, No. 2, Jan. 31, 2003.
Bailey, Mark J., et al., "Acyl glucuronide reactivity in perspective: biological consequences", Chemico-Biological Interactions, 2003, pp. 117-137.
Cook, Chyung S., et al., "Pharmacokinetics and metabolism of [14C] eplerenone after oral administration to humans", Drug Metabolism and disposition, 2003, vol. 31, No. 11, pp. 1448-1455.
Jurica, Jan, et al., "Determination of Cytochrome P450 Metabolic Activity Using Selective Markers", Topics on Drug Metabolism, 2012, pp. 191-220.
Prot, Jean-Matthieu, et al., "Performance of biotransformation of human primary hepatocytes exposed to a pharmacological cocktail inside a liver microchip", 14th International Conference on Miniaturized Systems for Chemisty and Life Sciences, Oct. 3-7, 2010, Groningen, The Netherlands, pp. 157-159.
International Search Report and Writtien Opinion for PCT/US2016/064210 dated Mar. 23, 2017.
International Preliminary Report on Patentability for PCT/US2016/064210 dated Jun. 14, 2018.
Begas, E., et al. "In vivo evaluation of CYP1A2, CYP2A6, NAT-2 and xanthine oxidase activities in a Greek population sample by the RP-HPLC monitoring of caffeine metabolic ratios." Biomedical Chromatography 21.2 (2007): 190-200.

(Continued)

*Primary Examiner* — Heidi Reese
(74) *Attorney, Agent, or Firm* — Quarles & Brady LLP

(57) ABSTRACT

Disclosed are methods and compositions which may be used in human cytochrome P450 (CYP450) enzyme phenotyping. The methods and compositions typically utilize a mélange of substrates for different CYP450 enzymes which may be administered orally to a patient. Subsequently, the metabolites of the substrates may be detected in the patient's saliva as well as any non-metabolized substrates to calculate a metabolic ratio for any given CYP450 enzyme in order to generate a phenotypic CYP450 enzyme profile for the patient.

18 Claims, 3 Drawing Sheets

(56) References Cited

OTHER PUBLICATIONS

Dorne, J. L. C. M., et al. "Uncertainty factors for chemical risk assessment: human variability in the pharmacokinetics of CYP1A2 probe substrates." Food and Chemical Toxicology 39.7 (2001): 681-696.

Frank, D., et al. "Evaluation of probe drugs and pharmacokinetic metrics for CYP2D6 phenotyping." European journal of clinical pharmacology 63.4 (2007): 321-333.

Hakooz 2009 Caffeine Metabolic Ratios for the In Vivo Evaluation of CYP1A2, N-acetyltransferase 2, Xanthine Oxidase and CYP2A6 Enzymatic Activities Current Drug Metabolism vol. 10, Issue 4, 329-338, 2009.

Nolin, T. D., et al. "Stereoselective determination of the CYP2C19 probe drug mephenytoin in human urine by gas chromatography—mass spectrometry." Journal of Chromatography B 783.1 (2003): 265-271.

Nyeki, A, et al. "Extractionless method for the simultaneous high-performance liquid chromatographic determination of urinary caffeine metabolites for N-acetyltransferase 2, cytochrome P450 1A2 and xanthine oxidase activity assessment." Journal of Chromatography B: Biomedical Sciences and Applications 755.1-2 (2001): 73-84.

Ou-Yang, D-S, et al. "Phenotypic polymorphism and gender-related differences of CYP1A2 activity in a Chinese population." British journal of clinical pharmacology 49.2 (2000): 145-151.

Rasmussen et al. 1998 Selective effects of somatostatin analogs on human drug-metabolizing enzymes. Clinical Pharmacology & Therapeutics, 64 2 150-159, 0009-9236.

Rendic, S.. "Summary of information on human CYP enzymes: human P450 metabolism data." Drug metabolism reviews 34.1-2 (2002): 83-448.

Takata, K., et al. "Phenotype-genotype analysis of CYP1A2 in Japanese patients receiving oral theophylline therapy." European journal of clinical pharmacology 62.1 (2006): 23-28.

Tassaneeyakul et al. 1994 Caffeine Metabolism by Human Hepatic Cytochromes P450—Contributions of 1a2, 2e1 and 3a Isoforms. Biochemical Pharmacology, 47 10 1767-1776, 0006-2952.

Tenneze et al. 1999 Assessment of CYP2D6 and CY2C19 activity in vivo in humans: A cocktail study with dextromethorphan and chloroguanide alone and in combination. Clinical Pharmacology & Therapeutics, 66 6 582-588, 0009-9236.

Van Troostwijk, Ljaed, et al. "Two novel methods for the determination of CYP1A2 activity using the paraxanthine/caffeine ratio." Fundamental & clinical pharmacology 17.3 (2003): 355-362.

Zanger, U. M., et al. "Cytochrome P450 2D6: overview and update on pharmacology, genetics, biochemistry." Naunyn-Schmiedeberg's archives of pharmacology 369.1 (2004): 23-37.

Zhou, S.-F. "Polymorphism of Human Cytochrome P450 2D6 and Its Clinical Significance." Clinical Pharmacokinetics 11.48 (2009): 689-723.

Donzelli, M., et al. "The basel cocktail for simultaneous phenotyping of human cytochrome P450 isoforms in plasma, saliva and dried blood spots." Clinical pharmacokinetics 53.3 (2014): 271-282.

Videau, O., et al. "Biochemical and analytical development of the CIME cocktail for drug fate assessment in humans." Rapid Communications in Mass Spectrometry 24.16 (2010): 2407-2419.

\* cited by examiner

COMPOSITIONS FOR CYP450 PHENOTYPING USING SALIVA SAMPLES

CROSS-REFERENCE TO RELATED PATENT APPLICATIONS

This application is the U.S. National Stage of International Application No. PCT/US2016/064210, filed on Nov. 30, 2016, and published as WO 2017/09521, on Jun. 8, 2017, which application claims the benefit of priority under 35 U.S.C. § 119(e) to U.S. Provisional Application No. 62/386,389, filed on Nov. 30, 2015, the contents of which applications are incorporated herein by reference in their entireties.

BACKGROUND

The field of the invention relates to medical diagnostics. More particularly, the field of the invention relates to pharmacogenetic medical diagnostics. More particularly, the field of the invention relates to a compositions which may be utilized in methods for multiple simultaneous metabolic enzyme phenotyping using a saliva sample.

Cytochrome P450 (CYP450) enzymes are responsible for much of the variability in drug response and toxicity susceptibility. The fields of pharmacogenetics and later pharmacogenomics began with observations that individuals from different racial/ethnic groups experienced different rates of response and toxicity to certain drugs. Scientists found significant differences in metabolic clearance of these 'highly variable' drugs on an individual and population level. They also found disproportionate frequencies of individuals with very low metabolic clearance amongst different racial/ethnic groups. Further investigations revealed genetic variants resulted in altered CYP450 enzyme activity and therefore differences in metabolic clearance of the drugs. After many years of investigation, CYP450 enzyme activity has remained the dominant determinant of metabolic clearance for many drugs. The CYP450 enzyme family is the most studied enzyme family in the field of pharmacogenetics.

When a drug is primarily metabolized via a specific CYP450 enzyme (i.e. responsible for 80% or more of drug clearance) it is known as a 'probe drug'. For these particular drugs, alterations in CYP450 enzyme activity results in significant differences in drug clearance. Differences in metabolic enzyme activity are quantified by measuring the metabolic ratio i.e. the concentration or area ratio of a known enzyme substrate divided by the primary metabolite. The metabolic ratio of the probe substrate is also called the metabolic phenotype although metabolic phenotype is often expressed as a categorical value such as poor metabolizer. Currently there are genetic assays which predict metabolic phenotype based on the presence or absence of genetic variants which result in altered metabolic clearance. The genetic predicted metabolic phenotypes are categorical and labeled relative to an average individual being labeled a rapid metabolizer. Other designations vary by CYP450 enzyme and particular study but common designations include: extensive metabolizer (EM) (i.e. the average wild type individual), poor metabolizer (PM) (i.e. individuals who have very poor metabolic clearance relative to the average wild type), intermediate metabolizer (IM) (i.e. individuals who have metabolic clearance between the average wild type and a poor metabolizer phenotype), rapid metabolizer (RM) (i.e. individuals who have higher metabolic clearance relative to the average wild type individual), and ultra-rapid metabolizers (UM) (i.e. individuals who have metabolic clearance significantly higher than rapid metabolizers).

Once the metabolic phenotype is determined, interventions such as lowering drug dosages in poor metabolizers can be performed. There is evidence showing benefits of genetic predicted phenotype guided drug dosing. However, there are some drawbacks to using genetic predicted phenotype. The genes encoding CYP450 enzymes do not change throughout a person's life but their level of expression, translation and activity do, thus the resulting metabolic phenotype is altered. A multitude of physiological and environmental factors such as alcohol ingestion, aging, diet, drug/pharmaceutical use producing enzyme induction or inhibition (drug-drug interactions), hepatic disease, renal disease, etc. impact the metabolic phenotype. In-vitro studies show a complex regulation of CYP450 activity including transcriptional regulation, translational regulation, post transcriptional modifications, and protein-protein interactions.

To avoid the pitfalls associated with genetic prediction of metabolic phenotype we have developed a composition, methods, and kit for the direct testing of metabolic phenotype for the major CYP450 enzymes using a mélange of extremely safe phenotyping probes with a non-invasive saliva based testing assay. This composition, methods, and kit allows for direct measurement of metabolic phenotype which can be converted into a traditional categorical phenotype or can be reported as a continuous variable metabolic phenotype.

SUMMARY

Disclosed are methods and compositions which may be used in cytochrome P450 (CYP450) enzyme phenotyping. The methods and compositions typically utilize a composition comprising one or more substrates for different CYP450 enzymes which may be administered orally to a patient. Subsequently, a metabolite of the one or more substrates may be detected in the patient's saliva as well as any non-metabolized substrate to calculate a metabolic ratio for any given CYP450 enzyme in order to generate a phenotypic CYP450 enzyme profile for the patient. The phenotypic CYP450 enzyme profile for the patient may be utilized in order to dose a drug for a patient and/or to assess hepatic function in the patient, for example, in a patient experiencing or at risk for developing hepatic failure.

DETAILED DESCRIPTION

Figure 1:
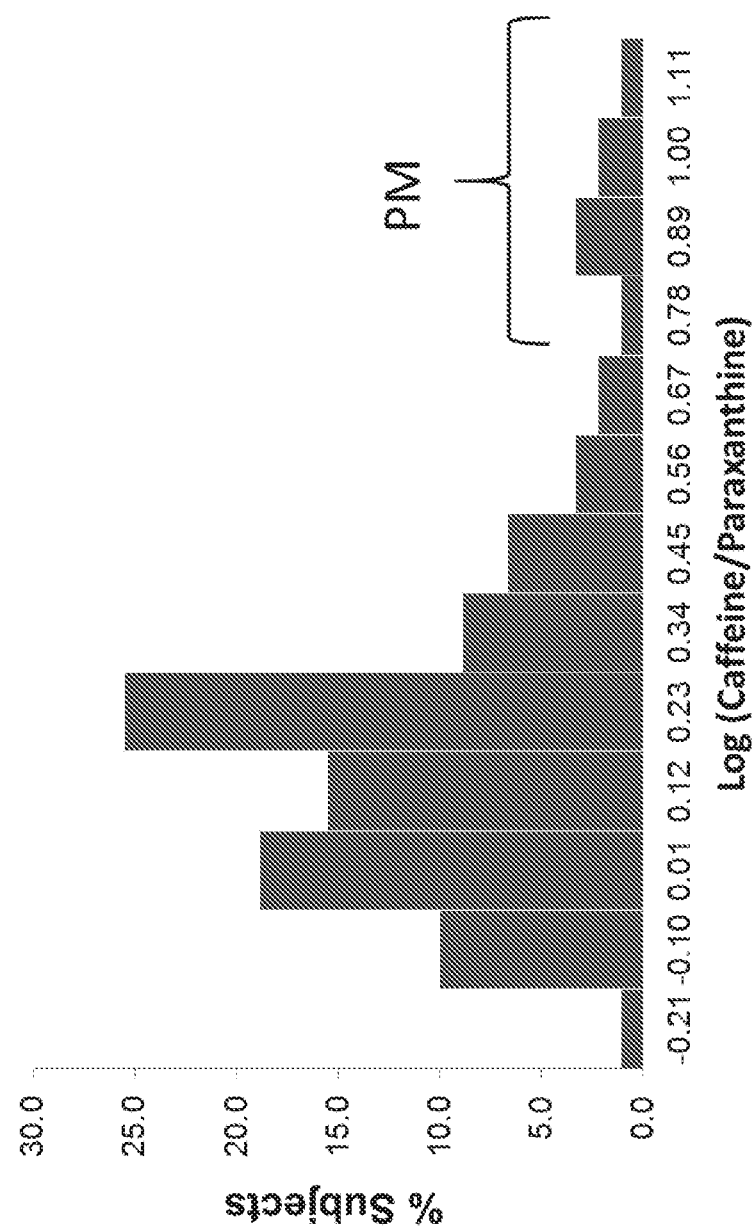
FIG. 1. Histogram of CYP1A2 Metabolic Phenotype in Healthy Adults.
Figure 2:
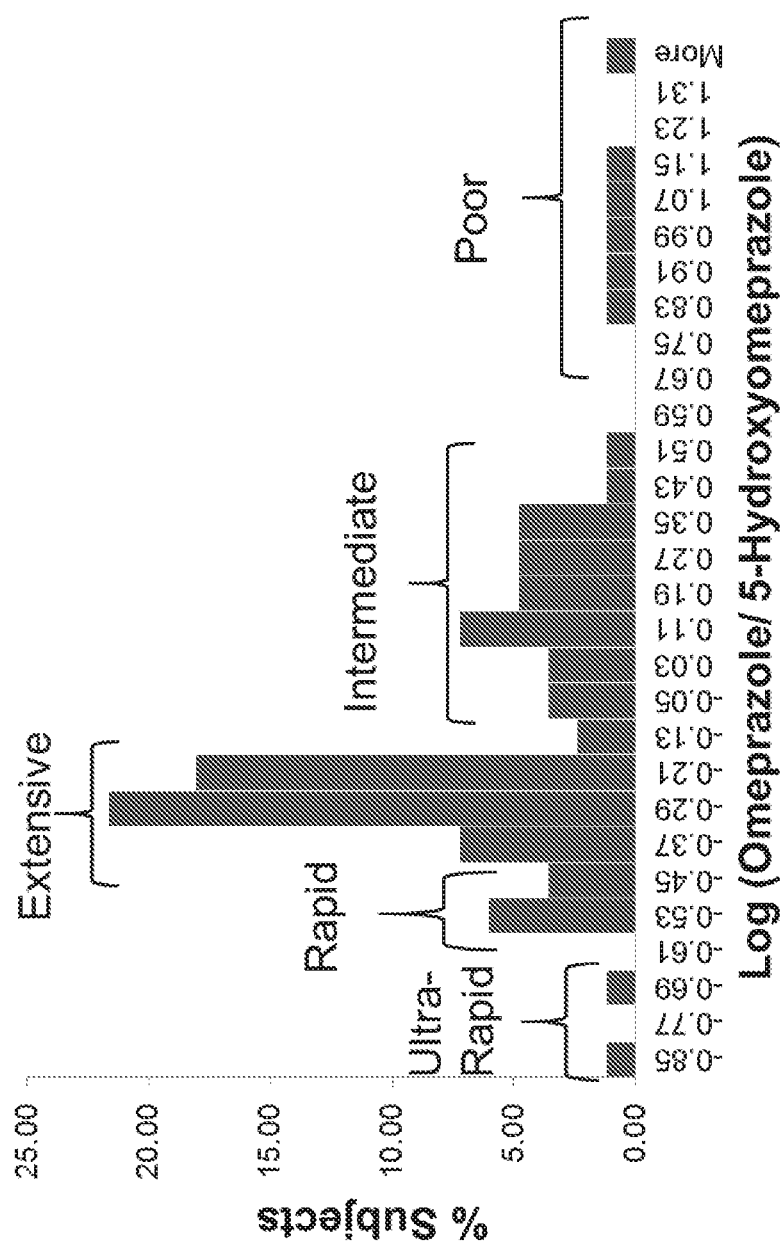
FIG. 2. Histogram of CYP2C19 Metabolic Phenotype in Healthy Adults.
Figure 3:
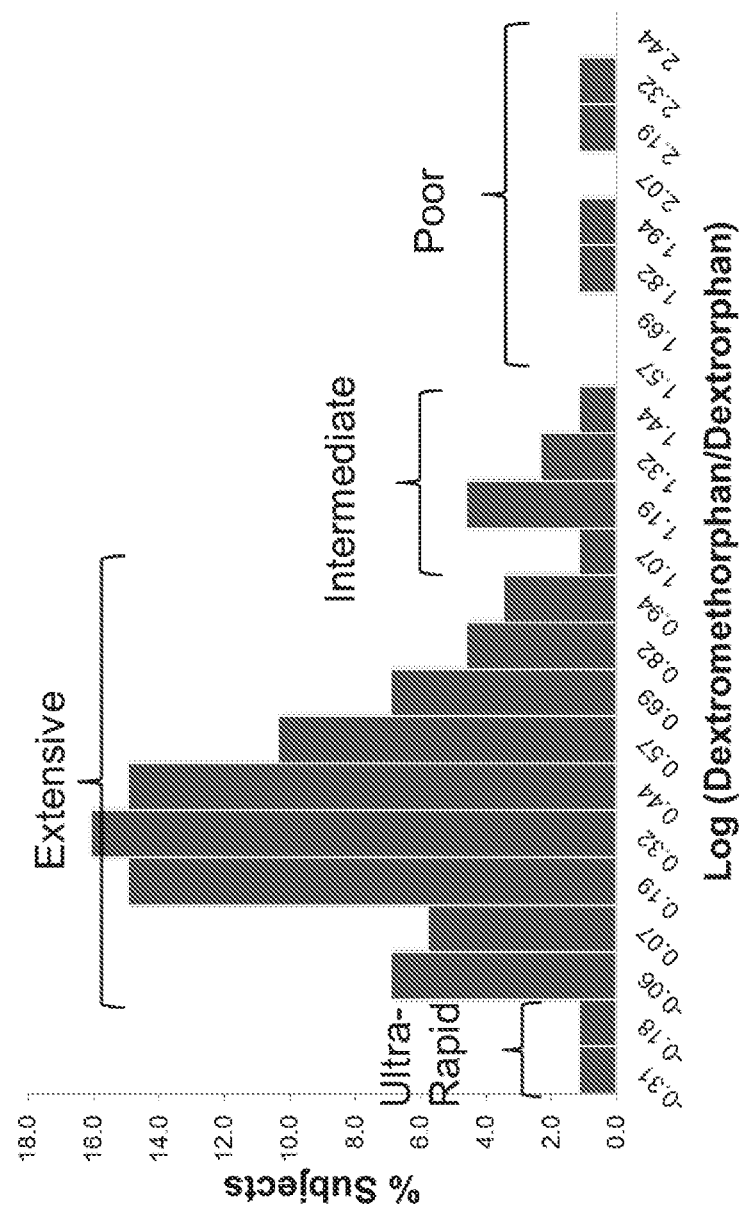
FIG. 3. Histogram of CYP2D6 Metabolic Phenotype in Healthy Adults.

The present invention is described herein using several definitions, as set forth below and throughout the application.

Unless otherwise specified or indicated by context, the terms "a", "an", and "the" mean "one or more." For example, "a substrate" and "a metabolite" should be interpreted to mean "one or more substrates" and "one or more metabolites," respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, "a patient in need thereof" may include a patient in need of phenotyping for cytochrome P450 (CYP450) enzymes. The term "patient" may be used interchangeably with the terms "subject" and "individual." A "patient" is intended to include human and non-human animals (e.g., non-human primates, dogs, cats, horses, and the like).

As used herein, "a patient in need thereof" may include a patient in need of drug dosing. As such, the disclosed methods may include methods for determining an appropriate dose for a drug for a patient based on the patient's phenotype for one or more cytochrome P450 (CYP450) enzymes, which phenotype may be determined as disclosed herein.

As used herein, "a patient in need thereof" may include a patient experiencing or at risk for developing hepatic failure. As such, the disclosed methods may include methods of assessing liver function in a patient experiencing or at risk for developing hepatic failure based on the patient's phenotype for one or more cytochrome P450 (CYP450) enzymes, which phenotype may be determined as disclosed herein.

As used herein, "a patient in need thereof" may include a patient enrolled in a drug study. As such, the disclosed methods may include methods of assessing liver function in a patient prior to participation in a drug study based on the patient's phenotype for one or more cytochrome P450 (CYP450) enzymes, which phenotype may be determined as disclosed herein.

The compositions disclosed herein typically include one or more substrates for one or more one or more isoforms of the cytochrome P450 (CYP450) enzymes. The disclosed compositions may include a mélange of substrates. As used herein, the term "mélange" means a mixture, and the terms "mélange" and "mixture" may be used interchangeably herein. A mélange may include a mixture of substrates for one or more enzymes. In particular, a mélange may include a mixture of substrates for one or more isoforms of the cytochrome P450 (CYP450) enzymes. The substrates of the mixture may be individually formulated into multiple formulations which may be administered substantially concurrently and/or the substrates of the mixture may be formulated together into a single formulation.

As used herein, a "substrate" refers to a chemical compound that is recognized by an enzyme and for which the enzyme catalyzes conversion of the substrate into a different chemical compound which may be referred to as a "metabolite." For example, the liver contains enzymes that convert various drug substances (i.e. substrates) to metabolites, which are eliminated from the body in urine or excrement. This enzyme conversion process often determines the duration of action or intensity of drugs, which is why some drugs may be taken several times each day to treat diseases and produce desirable pharmacological effects.

Liver enzymes may include isoforms of cytochrome P450 (CYP450), N-acetyl transferases, UDP-glucuronosyltransferases, oxidases sulfotransferases and other enzymes. Each of these enzyme systems may be comprised of numerous isoforms, each of which is capable of metabolizing different substrates. For example, the CYP450 system in the human liver includes at least ten individual isoforms. The CYP450 isoforms are often critical in determining the rate of elimination of drugs, and metabolism by CYP isoforms often represents the rate-limiting step in elimination of pharmaceuticals. Prediction of metabolic phenotype based exclusively on genetic analysis, genetic markers, and/or genetic deficiencies may produce an imprecise result due to failure to include environmental factors, concomitant disease, levels of CYP450 isoform expression, translation and activity, and other factors.

As such, a patient's ability to metabolize a pharmaceutical is an important factor in determining a proper dose or dose regimen for the pharmaceutical. Metabolic activity may be based on genetic markers including genetic deficiencies in a CYP450 isoform. As such, metabolic activity may be assessed by performing a genetic analysis.

However, an understanding of the patient's actual metabolic activity is the most important factor for determining a proper dose or dose regimen for the pharmaceutical. The methods disclosed herein may include determining a patient's methabolic phenotype and/or characterizing the patient's metabolic activity. A patient's metabolic activity may be referred to herein as a "metabolic phenotype." Based on a metabolic phenotype, a patient may be characterized as a poor metabolizer (PM), and intermediate metabolizer (IM), an extensive metabolizer (EM), or an ultra-rapid metabolizer (UM). For example, metabolic phenotypes may be generated by administering a substrate for an enzyme to the patient. Subsequently, a sample may be taken from the patient and analyzed for the presence of a metabolite and any unconverted substrate to calculate a metabolic ratio, which can be used to characterize the patient's metabolic activity.

Probe Mélange for Simultaneous CYP450 Phenotyping Using Saliva Samples

As such, disclosed herein are methods and compositions including mixtures which may be used in human cytochrome P450 (CYP450) enzyme phenotyping. The methods and compositions may include or utilize one or more substrates for one or more different CYP450 enzymes (e.g., one or more substrates for one or more of CYP1A2, CYP2C9, CYP2C19, CYP2E1, CYP2D6, CYP3A4, and CYP3A5) which may be administered orally to a patient. The substrates of the disclosed compositions may be administered orally to a patient. Subsequently, for example, after 0.5, 1.0, 1.5, 2.0, 2.5, 3.0, 3.5, 4.0, 4.5, 5.0, 5.5, 6.0, 7.0, 8.0, 9.0, 10.0, 11.0, 12.0, 24.0 hours or later, a saliva sample from the patient may be tested for a metabolite of one or more substrates of the composition that are metabolized by one or more CYP450 isoforms to generate the metabolite. The saliva sample from the patient also may be tested for any non-metabolized substrate. As such, a ratio of the concentration of metabolite/non-metabolized substrate in saliva from the patient may be calculated to generate a metabolic phenotype for the patient for one or more CYP450 isoforms.

In some embodiments, the disclosed methods include administering, typically orally, to a subject in need thereof a composition comprising one or more of: (i) a substrate for CYP1A2 ($SUB_{CYP1A2}$), wherein CYP1A2 catalyzes conversion of $SUB_{CYP1A2}$ to a metabolite ($MET_{CYP1A2}$); (ii) a substrate for CYP2C19 ($SUB_{CYP2C19}$), wherein CYP2C19 catalyzes conversion of $SUB_{CYP2C19}$ to a metabolite ($MET_{CYP2C19}$); (iii) a substrate for CYP2D6 ($SUB_{CYP2D6}$), wherein $CYP_{2D6}$ catalyzes conversion of $SUB_{CYP2D6}$ to a metabolite ($MET_{CYP2D6}$); and (iv) a substrate for CYP3A4 ($SUB_{CYP3A4}$), wherein CYP3A4 catalyzes conversion of $SUB_{CYP3A4}$ to a metabolite ($MET_{CYP3A4}$). Subsequently, the methods may include (b) detecting in a saliva sample from the subject one or more of: (i) $MET_{CYP1A2}$ and unconverted $SUB_{CYP1A2}$; (ii) $MET_{CYP2C19}$ and unconverted $SUB_{CYP2C19}$; (iii) $MET_{CYP2D6}$ and unconverted $SUB_{CYP2D6}$; and (iv) $MET_{CYP3A4}$ and unconverted $SUB_{CYP3A4}$.

In the disclosed methods, the composition administered to the patient may comprise one or more tablet formulations of one or more substrates selected from $SUB_{CYP1A2}$, $SUB_{CYP2C19}$, $SUB_{CYP2D6}$, and $SUB_{CYP3A4}$. In some embodiments, the composition includes multiple tablets, for example, one tablet each of $SUB_{CYP1A2}$, $SUB_{CYP2C19}$, $SUB_{CYP2D6}$, and $SUB_{CYP3A4}$. In other embodiments, the composition administered to the patient may comprise a single tablet formulation, the single table formulation including each of substrates including $SUB_{CYP1A2}$, $SUB_{CYP2C19}$, $SUB_{CYP2D6}$, and $SUB_{CYP3A4}$. Suitable tablet formulations may include immediate release tablet formulations, for example an immediate tablet release formulation for each of $SUB_{CYP1A2}$, $SUB_{CYP2C19}$, $SUB_{CYP2D6}$, and $SUB_{CYP3A4}$. In some embodiments, the tablet formulations may include a non-substrate coating (e.g., an enteric coating or other type of coating).

In some embodiments, the composition administered in the disclosed methods is a buffered composition. For example, the composition administered in the disclosed methods may include a basic buffering agent, which may include but is not limited to sodium bicarbonate and/or calcium carbonate.

In some embodiments, the composition administered in the disclosed methods has a basic pH when the composition is dissolved in water. For example, the composition administered in the disclosed methods may have a pH greater than about 7.5, 8.0, 8.5, or 9.0 when dissolved in water.

In the disclosed methods, the metabolites and/or the unconverted substrates may be detected in saliva using any suitable procedure. Suitable procedures may include but are not limited to procedures selected from the group consisting of Ultra High Pressure Liquid Chromatography (UHPLC), Mass Spectroscopy (MS), High Pressure Liquid Chromatography (HPLC), Ultraviolet Spectroscopy (UV), Gas Chromatography (GC), Electron Capture Detection (ECD), Flame Ionization Detection (FID), Raman Infrared (RI) Spectroscopy, Matrix-Assisted Laser Desorption/Ionization (MALDI), and combinations thereof. In addition, in the disclosed methods the metabolites and/or the unconverted substrates may be detected in saliva using reagent composition that include one or more reagents for detecting the metabolites and/or the unconverted substrates via reacting the saliva with the reagent compositions.

In the disclosed methods, the composition administered to the patient typically includes a substrate for one or more isoforms of CYP. In some embodiments, a substrate of the composition is a substrate for more than one isoform of CYP (e.g., a substrate for CYP1A2 may additionally be a substrate for another isoform of CYP such as any of CYP2C9, CYP2C19, CYP2E1, CYP2D6, CYP3A4, and CYP3A5). In other embodiments, a substrate of the composition is a substrate for one isoform of CYP and is not a substrate for another or any other isoform of CYP (e.g., a substrate for CYP3A4 may not be a substrate for another or any other of CYP1A2, CYP2C9, CYP2C19, CYP2E1, CYP2D6, and CYP3A5).

The substrates of the compositions that are administered in the disclosed methods may include "drugs" as known in the art. Preferably, the substrates (i.e., drugs) of the compositions that are administered in the disclosed methods and the metabolites of the substrates have suitable pharmaceutical characteristics such as oral bioavailability (e.g., greater than about 20%, 30%, 40% 50%, 60%, 70%, 80%, 90% or lower), and low or no plasma protein binding (e.g., less than about 90%, 80%, 70%, 60%, 50%, 40%, 30%, or 20%, or lower). Preferably, the substrates and the metabolites of the substrates have a suitable half-life which, in some embodiments, may be a half-life of greater than about 0.5, 1.0, or 2.0 hours and less than about 8.0, 7.0, 6.0, 5.0, or 4.0 hours (e.g., a half life of 2.0-4.0).

Suitable substrates for the compositions administered in the disclosed methods may include one or more drugs listed in the following Table of Exemplary Drugs:

| Table of Exemplary Drugs for Assessing Metabolism by CYP1A2. | | | | | |
|---|---|---|---|---|---|
| DRUG | ORAL BIOAVAILABILITY | PLASMA PROTEIN BINDING | HALF-LIFE (hrs) | MOLECULAR WEIGHT | METABOLISM |
| Amitriptyline | ~43-46% | >90% | ~13-36 | 277.4 | 2D6 |
| Clomipramine | 20-78% | 97% | 19-37 | 314.85 | 2C19, 3A4 |
| Imipramine | 22-77% | 60-96% | 8-21 | 280.41 | 2D6 |
| Agomelatine | <5% | 95% | 1-2 | 243.3 | |
| Clozapine | 12-81% | 97% | 4-66 | 326.82 | 2D6, 3A4 |
| Olanzapine | 87% | 93% | 21-54 | 312.43 | 2D6 |
| Haloperidol | 60% | 88.4-92.5% | 14-37 | 375.86 | 1A2, 2D6 |
| Caffeine | | 17-36% | 5 | 194.19 | |
| Ropivacaine | 87-98% - IV | 94% | 5-7 | 274.4 | |
| Theophylline | ~100% | 40% | 1.5-9.8 | 180.16 | 2E1 |
| Zolmitriptan | ~40% | 25% | 3 | 287.36 | |
| Melatonin | 3-76% | | 35-50 min | 232.28 | 1A1, 2C19 |
| Tamoxifen | | 99% | ~5-7 days | 371.51 | 2C9, 3A4, 3A5, 2C19, 2D6, 1A1, 3A7, 2B6, 2B1 |

-continued

Table of Exemplary Drugs for Assessing Metabolism by CYP1A2.

| DRUG | ORAL BIOAVAILABILITY | PLASMA PROTEIN BINDING | HALF-LIFE (hrs) | MOLECULAR WEIGHT | METABOLISM |
|---|---|---|---|---|---|
| Erlotinib | 60-100% | 93% | 36.2 | 393.44 | 3A4, 1A1, 1C |
| Cyclobenzaprine | 33-55% | 93% | 8-37 | 275.39 | 2D6, 3A4 |
| Estradiol | 43% | >95% | 36 hours | 272.38 | 3A4 |
| Fluvoxamine | 53-84% | ~77-80% | ~14-16 | 318.33 | |
| Mexiletine | 90% | 50-60% | 10-12 | 179.26 | 2D6 |
| Naproxen | 95% | >99% | 8-21 | 230.26 | 2C9, 2C8 |
| Ondansetron | 100% | 70-76% | 3-6 | 293.36 | 2D6, 3A4 |
| Phenacetin | | | | 179.22 | |
| Paracetamol | 85-98% | 10-25% | 1-4 | 151.16 | 2D6, 2E1 |
| Propranolol | 100% | >90% | 4 | 259.34 | 2D6 |
| Riluzole | ~60% | 96% | 12 | 234.2 | |
| Tacrine | 2.4-36% | 55% | 2-4 | 198.26 | |
| Tizanidine | 40% | 30% | 2.5 | 253.71 | |
| Verapamil | 20-35% | 90% | 2.8-7.4 | 454.6 | 2C8, 2C18, 2C9, 3A4, 3A5 |
| Warfarin | 100% | 99% | 20-60 | 308.33 | 2C9, 2C8, 2C18, 2C19, 1A1,, 3A4. |
| Zileuton | | 93% | 2.5-3.2 | 236.29 | 2C9, 3A4 |

Table of Exemplary Drugs for Assessing Metabolism by CYP2C9.

| DRUG | ORAL BIOAVAILABILITY | PLASMA PROTEIN BINDING | HALF-LIFE (hrs) | MOLECULAR WEIGHT | METABOLISM |
|---|---|---|---|---|---|
| Celecoxib | | 97% | 11 | 381.38 | |
| Lornoxicam | IM: 87% | 99.7% | 4 | 371.8 | |
| Diclofenac | 50% | >99% | 1.9-2.2 | 296.15 | |
| Ibuprofen | 87-100% | 99% | 1.8-2.44 | 206.3 | |
| Naproxen | 95% | >99% | 12-17 | 230.26 | |
| Ketoprofen | 90% | >99% | 2.1 | 254.29 | |
| Piroxicam | | 99% | 50 | 331.348 | |
| Meloxicam | 89% | 99.4% | 15-20 | 351.4 | |
| Suprofen | 92% | >99% | 2-4 | 260.3 | |
| Phenytoin | 20-90% | 88-93% | 14-22 | 274.25 | 2C9, 2C19 |
| Fluvastatin | 24% | 98% | 2.5 | 411.5 | 2C9, 2C8, 3A4 |
| Glipizide | 90-100% | 98-99% | 2.5 | 445.55 | |
| Glibenclamide | | 99% | 10 | 493.99 | |
| Glimepiride | 100% | >99% | 5-9.2 | 490.62 | |
| Tolbutamide | | 80-99% | 4.5-6.5 | 270.35 | |
| Glyburide | | 99% | 10 | 493.99 | |
| Irbesartan | 60-80% | 90% | 11-15 | 428.5 | |
| Losartan | 33% | 1.3% | 2 | 461 | 2C9, 3A4 |
| S-warfarin | 100% | 99% | 40 | 330.31 | 2C9, 2C19, 2C18, 1A2, 3A4 |
| Sildenafil | 41% | 96% | 4 | 666.7 | 3A4, 2C9 |
| Terbinafine | 40% | >99% | 22-26 | 327.9 | 2C9, 1A2, 3A4, 2C8, 2C19 |
| Amitriptyline | 30-60% | >90% | 15 | 313.87 | 3A4, 2C9, 2D6, 1A2, 2C19 |
| Fluoxetine | 60-80% | 94.5% | 4-6 days | 309.3 | 2D6, 2C9 |
| Nateglinide | 73% | 98% | 1.5 | 317.423 | 2C9, 3A4 |
| Rosiglitazone | 99% | 99.8% | 3-4 | 357.4 | 2C8, 2C9 |
| Tamoxifen | | 99% | 5-7 days | 371.5 | 3A, 2C9, 2D6 |
| Torasemide | 80% | >99% | 2.2-3.8 | 348.43 | |
| Ketamine | IM: 90-93%, PO: 16% | 47% | 2-3 | 274.19 | |
| THC | 10-35% | 97-99% | 1.6-59 | 314.469 | 2C9, 2C19, 3A4 |
| Limonene | | | | 136.24 | 2C9, 2C19 |
| Tapentadol | 32% | 20% | 4-5 | 257.8 | 2C9, 2D6 |
| Polyunsaturated FAs | 64-73% | >99% | 2.7-5.5 | 608.18 | 2C8, 2C9, 3A4 |
| Montelukast | | | | | |

Table of Exemplary Drugs for Assessing Metabolism by CYP2C19.

| DRUG | ORAL BIOAVAILABILITY | PLASMA PROTEIN BINDING | HALF-LIFE (hrs) | MOLECULAR WEIGHT | METABOLISM |
|---|---|---|---|---|---|
| Amitriptyline | 30-60% | >90% | 15 | 313.87 | 3A4, 2C9, 2D6, 1A2, 2C19 |
| Clomipramine | 20-78% | 97% | 32 | 351.3 | |
| Imipramine | 94-96% | 89% | 6-18 | 316.9 | 2C19, 2D6 |
| Citalopram | 80% | 80% | 35 | 324.4 | 3A4 |
| Moclobemide | 55-95% | 50% | 2 | | |
| Bupropion | | 84% | 19-21.3 | 276-320 | 2B6 |
| Diazepam | 98% | 95-99.3% | Up to 48 | 284.75 | 3A4 |
| Mephenytoin | "Well-absorbed" | 59.6% | 17 | 218.25 | |
| Nordazepam | | | 36-200 | 270.7 | |
| Phenytoin | 20-90% | 88-93% | 14-22 | 274.25 | 2C9 |
| Phenobarbital | 80-100% | 20-60% | 36-120 | 232.24 | |
| Primidone | 90-100% | 20-30% | 3.3-7 | 218.25 | |
| Hexobarbital | | 25% | | 236.3 | 2C9 |
| Methylphenobarbital | 50% | 70-76% | 31-67 | 246.3 | |
| Llansoprazole | 81-91% | 97-99% | 0.9-1.5 | 369.37 | 1A2 |
| Omeprazole | 30-40% | 95-96% | 0.5-1 | 345.42 | |
| Pantoprazole | 77% | 98% | 1 | 405-432 | 3A4, 2D6, 2C9 |
| Rabeprazole | 52% | 96.3% | 1-2 | 381.43 | 3A |
| Esomeprazole | 90% | 97% | 1.5 | 367.4 | 3A4 |
| Clopidogrel | >50% | 98% | 6 | 419.9 | 3A, 2B6, 1A2 |
| Proguanil | | 75% | 12-18 | 253.7 | |
| Propranolol | 30-70% | 93% | 3-6 | 295.8 | |
| Limonene | | | 12-24 | 136.26 | |
| Gliclazide | 80% | 85-99% | 8-12 | 323.4 | |
| Carisoprodol | | 60% | 8 | 260.3 | |
| Chloramphenicol | 90-100% | 50-80% | 1.6-3.3 | 323.13 | |
| Cyclophosphamide | >75% | >60% | 3-12 | 279.1 | |
| Indomethacin | 100% | 99% | 4.5 | 357.8 | |
| Nelfinavir | | 98% | 3.5-5 | 567.78 | 3A, 2C19 |
| Nilutamide | | 80-84% | 38-59.1 | 317.2 | |
| Progesterone | 10-15% | 95-99% | PV: 5-20 min | 314.5 | |
| Teniposide | | >99% | 5 | 656.6 | |
| Warfarin | 100% | 99% | 40 | 330.31 | 2C9, 2C19, 2C18, 1A2, 3A4 |
| Tapentadol | 32% | 20% | 4-5 | 257.8 | 2C9, 2C19 |

Table of Exemplary Drugs for Assessing Metabolism by CYP2D6.

| DRUG | ORAL BIOAVAILABILITY | PLASMA PROTEIN BINDING | HALF-LIFE (hrs) | MOLECULAR WEIGHT | METABOLISM |
|---|---|---|---|---|---|
| Imipramin | 94-96% | 89% | 6-18 | 316.9 | 2C19, 2D6 |
| Amitriptyline | ~43-46% | >90% | ~13-36 | 277.4 | 3A4, 2C9, 2D6, 1A2, 2C19 |
| Fluoxetine | 60-80% | 94.5% | 4-6 days | 309.3 | 2D6, 2C9 |
| Paroxetine | | 93-95% | 15-21 | 329.3 | |
| Fluvoxamine | 53% | 80% | 15.6 | 318.3 | 1A2, 2C9, 2C19, 2D6, 3A4 |
| Venlafaxine | 12.6% | 27-30% | 5 | 277 | |
| Duloxetine | 30-80% | >90% | 12 | 333.88 | 1A2, 2D6 |
| Mianserin | 20-30% | 90% | 1.4 | 264.4 | |
| Mirtazapine | 50% | 85% | 26-37 | 265.36 | 2D6, 1A2, 3A4 |
| Codeine | 90% | 7-25% | 2.5-3 | 299.36 | 2D6, 3A4 |
| Tramadol | 75% | 20% | 5.6-5.7 | 299.8 | 2D6, 3A4 |
| O-desmethyltramadol | | | 9 | 249.349 | M1 |
| N-desmethyltramadol [inactive] | | | | | |
| Oxycodone | 60-87% | 45% | 5.6 | 315.37 | 3A4, 2D6 |
| Hydrocodone | 25% | 19-45% | 7-9 | 494.5 | 3A4, 2D6, 2C19, 2B6 |
| Tapentadol | 32% | 20% | 4-5 | 257.8 | 2C9, 2D6 |
| Haloperidol | 60% | 88.4-92.5% | 14-37 | 375.86 | 1A2, 2D6 |
| Risperidone | 70% | 90% | 3-20 | 410.49 | |
| Perphenazine | 20% | | 9-12 | 403.97 | |
| Thioridazine | | | 21-24 | 370.577 | |
| Zuclopenthixol | 49% | 98% | 20 | 400.965 | 2D6, 3A4 |
| Iloperidone | 96% | 95% | 18-33 | 426.48 | 3A4, 2D6 |
| Aripiprazole | 87% | >99% | 75 | 448.38 | 2D6, 3A4 |
| Chlorpromazine | 32% | 90-99% | 6 | 318.86 | |
| Levomepromazine | 50-60% | | 15 | 328.5 | |
| Remoxipride | 96% | 5-6% | 3-6 | 371.27 | |
| Minaprine | | | 2-2.5 | 298.38 | |

-continued

Table of Exemplary Drugs for Assessing Metabolism by CYP2D6.

| DRUG | ORAL BIOAVAILABILITY | PLASMA PROTEIN BINDING | HALF-LIFE (hrs) | MOLECULAR WEIGHT | METABOLISM |
|---|---|---|---|---|---|
| Tamoxifen | | 99% | 5-7 days | 371.5 | 3A, 2C9, 2D6 |
| Metoprolol | 77% | 12% | 3-7 | 652.8 | |
| Timolol | 90% | <10% | 4 | 316.4 | |
| Alprenolol | 20% | 80% | 2-3 | 249.34 | |
| Carvedilol | 25-35% | 95-98% | 6-10 | 406.5 | 2D6, 2C9, 3A4, 2C19, 1A2 |
| Bufuralol | | | | 297.8 | |
| Nebivolol | 12-96% | 98% | 12-19 | 441.9 | |
| Propranolol | 30-70% | 93% | 3-6 | 295.8 | |
| Debrisoquine | | | | 448.5 | |
| Flecainide | 70-95% | 40% | 20 | 474.4 | |
| Propafenone | 3.4-10.6% | >95% | 2-10 | 377.92 | 2D6, 3A4, 1A2 |
| Encainide | 25-90% | 70.5-78% | 1.5-11.3 | 352.47 | |
| Mexiletine | 80-90% | 50-70% | 6-17 | 179.259 | 2D6, 1A2 |
| Lidocaine (mainly by 3A4) | 35% | 60-80% | 1.5-2 | 234.34 | 1A2, 3A4, 2D6 |
| Sparteine | | | | 234.38 | |
| Ondansetron | 56% | 70-76% | 3-6.2 | 293.4 | |
| Donepezil | 100% | 96% | 70 | 379.5 | 2D6, 3A4 |
| Phenformin | 40-60% | 12-20% | 4-13 | 205.26 | |
| Tropisetron | 60-100% | 71% | 5.6-8.6 | 284.4 | |
| Amphetamine | 100+% | 20% | 11-12.36 | 135.21 | |
| Methoxyamphetamine | | | | 165.232 | |
| Dextromethamphetamine | | | 12 | 149.24 | |
| Atomoxetine | 63% | 98% | 5.2 | 291.82 | |
| Chlorphenamine | 25-50% | 72% | 20 | 274.8 | |
| Dexfenfluramine | 68% | 36% | 17-20 | 231.257 | |
| Dextromethophan | 11% | | 1.4-3.9 | 370.33 | 2D6, 3A4, 3A5 |
| Metoclopramide | 80% | 30% | 5-6 | 354.3 | |
| Perhexiline | | | 12-18 | 277.488 | |
| Phenacetin (analgesic) | | | | 179.216 | |
| Promethazine | 88% | 93% | 16-19 | 284.42 | |

Table of Exemplary Drugs for Assessing Metabolism by CYP3A4.

| DRUG | ORAL BIOAVAILABILITY | PLASMA PROTEIN BINDING | HALF-LIFE (hrs) | MOLECULAR WEIGHT | METABOLISM |
|---|---|---|---|---|---|
| Alfentanil (Alfenta) | | 92% | 1.5 | 452.98 | |
| Alfazosin (Uroxatral) | 49% | 86% | 10 | 425.9 | |
| Almortriptan (Axert) | 70% | 35% | 3.5 | 469.56 | 2D6, MAO |
| Alprazolam (Xanax) | 90% | 80% | 11 | 308.76 | |
| Amiodarone (Cordarone) | 50% | 96% | >9 days | 681.78 | 2C8 |
| Amlodipine (Norvasc) | 64-90% | 93% | 30-60 | 567.1 | |
| Aprepitant (Emend) | 60-65% | 95% | 9-13 | 534.4 | 1A2, 2C19, 2C9 |
| Atazanavir (Reyataz) | 60-68% | 86% | 7 | 704.9 | |
| Atorvastatin (Lipitor) | 14% | 98% | 7-14 | 558.6 | |
| Bepridil (Vascor) | 60% | 99-100% | 42 | 366.5 | |
| Bexarotene (Targretin) | | 99% | 7 | 348.5 | |
| Basentan (Tracleer) | 50% | 98% | 5 | 551.6 | 2C9 |
| Bromocriptine (Parlodel) | 65-95% | 90-96% | 6-20 | 654.6 | |
| Budesonide (Entocort) | 9-21% | 85-90% | 2-3.6 | 430.5 | |
| Buprenorphine (Subutex) | 46-65% | 96% | 24-48 | 467.6 | |
| Bupropion (Zyban, Wellbutrin, Voxra) | | 84% | 19-21.3 | 239.7 | 2B6 |
| Carbamazepine (eg. Tegretol) | 89% | 76% | 12-17 | 236.3 | |
| Cevimeline (Evoxac) | | <20% | 4-6 | 199.3 | 2D6, 3A3 |
| Cilostazol (Pletal) | 87-100% | 95-98% | 11-13 | 369.5 | 2C19 |
| Cisapride (Propulsid) | 35-65% | 98% | 6-12 | 465.9 | |
| Clarithromycin (Biaxin) | 55% | Low | 4 | 747.9 | |
| Clonazepam (Klonopin) | 90% | 85% | 30-40 | 315.7 | |
| Clopidogrel (Plavix) | >50% | 94-98% | 6 | 321.8 | 2C19, 3A, 2B6, 1A2 |
| Colchicine | 45% | 39% | 26.6-31.2 | 399.4 | |
| Cyclophosphamide (Cytoxan) | >75% | >60% | 3-12 | 261.1 | |
| Cyclosporine (Neoral) | 30% | 90% | 19 | 1202.6 | |
| Dapsone (Avlosulfon) | 86-104% | 70-90% | 10-50 | 248 | |
| Darunavir (Prezista) | 37% | 95% | 15 | 593.73 | |
| Dasatinib (Sprycel) | | 96% | 3-5 | 488.01 | |
| Delavirdine (Rescriptor) | 85% | 98% | 5.8 | 552.68 | 3A, 2D6 |
| Dexmethasone (Decadron) | 86.10% | 77% | 1.88-2.23 | 392.47 | |
| Dihydroergotamine | <32% | 93% | 9-10 | 679.8 | |

-continued

Table of Exemplary Drugs for Assessing Metabolism by CYP3A4.

| DRUG | ORAL BIOAVAILABILITY | PLASMA PROTEIN BINDING | HALF-LIFE (hrs) | MOLECULAR WEIGHT | METABOLISM |
|---|---|---|---|---|---|
| Diltiazem (Cardizem) | >40% | 70-80% | 3-6 | 450.99 | |
| Disopyramide (Norpace) | 80% | 50-65% | 6.7 | 437.47 | |
| Docetaxel (Taxotere) | 8% | 94-97% | 11.1 | 861.9 | |
| Donepezil (Aricept) | 100% | 96% | 70 | 379.5 | 3A4, 2D6 |
| Doxorubicin (Adriamycin) | 5% | 74-76% | 20-48 | 579.99 | |
| Droperidol | | | 2 | 379.43 | |
| Dutasteride (Avodart) | 60% | 99% | 5 weeks | 528.5 | |
| Ebastine (Kestine) | "High" | 98% | 24.8 | 469.658 | |
| Efavir enz (Sustiva) | 40-45% | 99.5-99.75% | 40-55 | 315.675 | 3A, 2B6 |
| Eletriptan (Relpax) | 50% | 85% | 4 | 463.4 | |
| Eplerenone (Inspra) | 69% | 50% | 3-6 | 414.5 | |
| Ergotamine (Ergomar) | <5% | | 1.5-2.5 | 581.66 | |
| Erlotinib (Tarceva) | 60% | 93% | 36.2 | 393.436 | 3A4, 1A2 |
| Erythromycin | 30-65% | 90% | 1-1.5 | 744.94 | |
| Estazolam (ProSom) | 93% | 93% | 10-24 | 294.74 | |
| Eszopiclone (Lunesta) | | 52-59% | 6 | 388.808 | 3A4, 2E1 |
| Ethinyl Estradiol | 38-48% | 97-98% | 7-36 | 296.403 | |
| Ethosuximide (Zarontin) | 93% | | 25-60 | 141.168 | 3A4, 2E1 |
| Etoposide (Vepesid) | 50% | 97% | 7 | 588.57 | |
| Exemestane (Aromasin) | 42% | 90% | 24 | 295.41 | |
| Felodipine (Plendil) | 13-20% | 99% | 26.7-33.2 | 384.259 | |
| Fentanyl (Sublimaze) | 76-92% | 80-86% | 3-27 | 336.5 | |
| Finasteride (Proscar) | 65% | 90% | 4.5 | 372.55 | |
| Flurazepam (Dalmane) | 83% | 97.2% | 2.3 | 387.9 | |
| Fosamprenavir (Lexiva) | | 90% | 7.7 | 585.608 | |
| Galantamine (Reminyl) | 90% | 18% | 7 | 368.27 | 3A4, 2D6 |
| Gefitinib (Iressa) | 60% | 90% | 48 | 446.9 | 3A4, 2D6 |
| Granisetron (Kytril) | 60% | 65% | 3-24 | 312.4 | 1A1, 3A |
| Halofantrine (Halfan) | | 60-70% | 6-10 days | 500.423 | |
| Ifosfamide (Ifex) | 92-100% | 20% | 7 | 261.1 | 3A, 2B1, 2B6 |
| Imatinib (Gleevec) | 98% | 95% | 18 | 589.7 | |
| Indinavir (Crixivan) | 30% | 60% | 1.8 | 711.88 | |
| Irinotecan (Camptosar) | | 30-68% | 6-12 | 677.19 | |
| Isradipine (DynaCirc) | IR 90-95%; CR: 15-24% | 95% | 8 | 371.39 | |
| Itraconazole (Sporanox) | 55% | 99.8% | 35-64 | 705.64 | |
| Ixabepilone (Ixempra) | | 67-77% | 52 | 506.7 | |
| Ketoconazole (Nizoral) | 75% | 99% | 2-8 | 531.43 | |
| Lapatinib (Tykerb) | | >99% | 24 | 581.1 | 3A4, 3A5 |
| Levomethadyl (Orlaam) | | 80% | 35-60 | 353.5 | |
| Loperamide (Imodium) | 0.30% | 97% | 9-14 | 477 | |
| Lopinavir (Kaletra) | | 98-99% | 5-6 | 628.8 | |
| Loratadine (Claritin) | 100% | 97% | 8 | 382.9 | 2D6, 3A4 |
| Lovastatin (Mevacor) | 5% | >95% | 2-5 | 404.5 | 3A, 2C8 |
| Maraviroc (Selzentry) | 23-33% | 76% | 14-18 | 513.67 | |
| Mefloquine (Lariam) | 85% | 98% | 3 weeks | 414.78 | |
| Methylprednisolone | | 78% | 2-3 | 374.5 | |
| Midazolam (Versed) | PO: 36% | 97% | 3-6 | 362.25 | |
| Mifepristone (Mifeprex) | 69% | 99.2% | 20-85 | 429.6 | |
| Modafinil (Provigil) | | 60% | 7.5-15 | 273.35 | |
| Nefazodone | 20% | >99% | 2-4 | 506.5 | |
| Nevirapine (Viramune) | 80-94% | 60% | 25-45 | 266.3 | 3A4, 2B6 |
| Nicardipine (Cardene) | 35% | >95% | 8.6-14.4 | 515.99 | 3A4, 2C8, 2D6 |
| Nifedipine (Adalat) | 45-56% | 92-98% | 2 | 346.3 | |
| Nimodipine (Nimotop) | 13% | >95% | 8-9 | 418.4 | |
| Nisoldipine (Sular) | 5% | 99% | 13.7 | 388.4 | |
| Nitrendipine (Baypress) | 23% | 97-99% | 2-24 | 360.4 | |
| Oxybutynin (Ditropan) | | 91-93% | 7-30 | 357.5 | |
| Oxycodone (Percodan) | 60-87% | 45% | 5.6 | 315.37 | 3A4, 2D6 |
| Paclitaxel (Taxol) | 6.50% | 89-98% | 13.1-52.7 | 853.9 | 2C8, 3A4 |
| Paricalcitol (Zemplar) | 72% | 99.8% | 5-7 | 416.6 | |
| Pimozide (Orap) | 50% | | 55 | 461.56 | 3A4, 1A2, 2D6 |
| Pioglitazone | 50% | >99% | 3-7 | 392.9 | 3A4, 2C8 |
| Praziquantel (Biltricide) | 80% | 80% | 0.8-3 | 312.4 | |
| Prednisolone | 77.6-84.5% | 70-90% | 2-4 | 360.4 | |
| Prednisone | 92% | 70% | 2-3 | 358.43 | |
| Propoxyphene (Darvon) | 40% | 78% | 6-12 | 339.5 | |
| Quazepam (Doral) | 29-35% | >95% | 25-41 | 386.8 | |
| Quetiapine (Seroquel) | 100% | 83% | 6-7 | 883.1 | |
| Quinacrine | | 80-90% | 5 days | 399.96 | |
| Quinidine | 70-80% | 50-88% | 6-8 | 324.43 | |
| Quinine | 76-88% | 69-92% | 9.7-20 | 782.96 | |
| Ranulazine (Ranexa) | 55% | 62% | 7-8.9 | 427.54 | 3A, 2D6 |

Table of Exemplary Drugs for Assessing Metabolism by CYP3A4.

| DRUG | ORAL BIOAVAILABILITY | PLASMA PROTEIN BINDING | HALF-LIFE (hrs) | MOLECULAR WEIGHT | METABOLISM |
|---|---|---|---|---|---|
| Repaglinide (Prandin) | 56% | >98% | 1 | 452.6 | 3A4, 2C8 |
| Rifabutin (Rimactane) | 53% | 85% | 36-45 | 847.02 | |
| Ritonavir (Norvir) | | 98-99% | 3-5 | 720.95 | 3A4, 2D6 |
| Saquinavir (Invirase) | | 98% | 13 | 670.86 | |
| Sibutramine (Meridia) | 77% | 97% | 1.1 | 334.33 | |
| Sildenafil (Viagra) | 41% | 96% | 4 | 666.7 | 3A4, 2C9 |
| Simvastatin (Zocor) | <5% | 95% | 2.8-3.26 | 418.57 | |
| Sirolimus (Rapamune) | 14-27% | 92% | 61.3-72.3 | 914.2 | |
| Solifenacin (Vesicare) | 90% | 98% | 45-68 | 362.5 | |
| Sufentanil (Sufenta) | | 93% | 2.5 | 578.68 | |
| Sunitinib (Sutent) | | 95% | 40-60 | 532.6 | |
| Tacrolimus (Prograf) | 17-31% | 99% | 8.7-37.9 | 822.03 | |
| Tadalafil (Cialis) | | 94% | 15-35 | 389.41 | |
| Tamoxifen (Nolvadex) | | 99% | 5-7 days | 371.5 | 3A4, 2C9, 2D6 |
| Tamsulosin (Flomax) | >90 | 94-99% | 9-15 | 444.98 | 3A4, 2D6 |
| Teniposide (Vumon) | | >99% | 5 | 656.7 | |
| Testosterone | Varies | 98% | varies | 288.4 | |
| Tiagabine (Gabitril) | 90% | 96% | 7-9 | 412 | 3A, 1A2, 2D6, 2C19 |
| Tinidazole (Tindamax) | 100% | 12% | 11.1-14.7 | 247.3 | |
| Tipranavir (Aptivus) | 30?% | 99.9% | 5.5-6 | 602.7 | |
| Topiramate (Topamax) | 80% | 15-41% | 21 | 339.36 | |
| Triazolam (Halcion) | | 89-94% | 2.3 | 343.21 | |
| Vardenafil (Levitra) | 15-44% | 95% | 4-5 | 579.1 | 3A4, 3A5, 2C |
| Verapamil (Calan) | 13-65% | 86-94% | 4-12 | 491.1 | 3A4, 1A2, 2C8, 2C9, 2C18 |
| Vinblastine (Velbane) | | 98-99.7% | 24.8 | 909.06 | |
| Vincristine (Oncovin) | | | 85 | 923.04 | |
| Ziprasidone (Geodon) | 60% | >99% | 7 | 467.42 | 3A4, 1A2 |
| Zolpidem (Ambien) | 70% | 92.5% | 2.5-2.8 | 764.9 | |
| Zonisamide (Zonegran) | | 40-60% | 63 | 212.23 | |
| Zopiclone (Imovane) | 80% | 45% | 3.5-6.5 | 388.8 | |

In the disclosed methods, the composition administered to the patient may include a substrate for CYP isoform 1A2 ($SUB_{CYP1A2}$). In some embodiments, the substrate for CYP1A2 ($SUB_{CYP1A2}$) is also a substrate for additional enzymes such as additional CYP isoforms such as isoform 2A6 or other enzymes such as N-acetyl transferases (NATs) and/or xanthine oxidases (XOs). In some embodiments, the substrate for CYP isoform 1A2 is also a substrate for each of CYP1A2, CYP2A6, NAT, and XO. Suitable substrates for CYP1A2 may include but are not limited to caffeine (e.g., where the metabolite ($MET_{CYP1A2}$) is paraxanthine) and theophylline.

In the disclosed methods, the composition administered to the patient may include a substrate for CYP isoform 2C19 ($SUB_{CYP2C19}$). In some embodiments, the substrate for CYP2C19 also is a substrate for additional enzymes such as additional CYP isoforms such as isoform 3A4 ($SUB_{CYP3A4}$). Suitable substrates for CYP2C19 may include but are not limited to omeprazole (e.g., where the metabolite ($MET_{CYP2C19}$) is 5OH-omeprazole), esomeprazole, mephenytoin, clopidogrel, and phenytoin. In some embodiments, the composition administered to the patient includes omeprazole and a basic buffering agent, which may include but is not limited to sodium bicarbonate and/or calcium carbonate.

In the disclosed methods, the composition administered to the patient may include a substrate for CYP isoform 2D6 ($SUB_{CYP2D6}$). Suitable substrates for CYP2D6 may include but are not limited to dextromethorphan (e.g., where the metabolite ($MET_{CYP2D6}$) is dextrorphan), desipramine, and metoprolol.

In the disclosed methods, the composition administered to the patient may include a substrate for CYP isoform 3A4 ($SUB_{CYP3A4}$), for example, wherein a metabolite ($MET_{CYP3A4}$) is subsequently detected in saliva of the patient and any unmetabolized $SUB_{CYP3A4}$. Suitable substrates for CYP3A4 may include but are not limited to eplerenone (e.g., where the metabolite ($MET_{CYP33A4}$) is 6-hydroxyeplerenone and/or 21-hydroxyeplerenone), midazolam, simvastatin, alfentanil, dextromethorphan, omeprazole, erythromycin, cortisol, midazolam, quindine, and triazolam.

In the disclosed methods, the composition administered to a patient may include a mixture of substrates comprising one or more of $SUB_{CYP1A2}$, $SUB_{CYP2C19}$, $SUB_{CYP2D6}$, and $SUB_{CY3A4}$. In some embodiments of the disclosed methods, the composition administered to the patient further includes a substrate for an enzyme selected from one or more of CYP2C9, CYP2E1, and CYP3A5 (i.e., $SUB_{CYP2A9}$, $SUB_{CYP2E1}$, and $SUB_{CY3A5}$, respectively).

In the disclosed methods, the composition administered to the patient include may include a substrate for CYP isoform 2C9 ($SUB_{CYP2C9}$), for example, wherein a metabolite ($MET_{CYP2}C9$) is subsequently detected in saliva of the patient and any unmetabolized $SUB_{CYP2C9}$. Suitable substrates for CYP2C9 may include but are not limited to warfarin, tolbutamide, diclofenac, flurbiprofen, celecoxib, lornoxicam, ibuprofen, naproxen, ketoprofen, piroxicam, meloxicam, suprofen, phenytoin, fluvastatin, glipizide, glibenclamide, glimepiride, glyburide, irbesartan, losartan, S-warfarin, sildenafil, terbinafine, amitriptyline, fluoxetine, nateglinide, rosiglitazone, tamoxifen, torasemide, ketamine, THC, JWH-018, AM-2201, and limonene.

In the disclosed methods, the composition administered to the patient include may include a substrate for CYP isoform 2E1 ($SUB_{CYP2E1}$), for example, wherein a metabolite ($MET_{CYP2E1}$) is subsequently detected in saliva of the patient and any unmetabolized $SUB_{CYP2E1}$. Suitable substrates for CYP2E1 may include but are not limited to chlorzoxazone, desipramine, and metoprolol.

In the disclosed methods, the composition administered to the patient include may include a substrate for CYP isoform 3A5 ($SUB_{CYP3}A5$), for example, wherein a metabolite ($MET_{CYP3A5}$) is subsequently detected in saliva of the patient and any unmetabolized $SUB_{CYP3A5}$. Suitable substrates for CYP3A5 may include but are not limited to alprazolam (α-hydroxylation), cortisol, alfentanil, midazolam, tacrolimus, and triazolam, and vincristine.

In the disclosed methods, the composition administered to the patient may include a substrate for additional enzymes which are not CYP isoforms. In some embodiments of the disclosed methods a mixture of substrates administered to the patient may include a substrate for an enzyme selected from a group consisting of an N-acetyl transferase (NAT), a methyl transferase, a UDP glucuronosyl transferase (UGT), a sulfo transferases, and an oxidative enzyme, or a combination thereof. In some embodiments of the disclosed methods, a mixture of substrates administered to the patient may include a substrate for an isoform of UDP glucuronosyl transferase (UGT), which may include, but is not limited to a substrate for one or more of UGT1A1, UGT1A4, UGT1A6, UGT1A9, and UGT2B7.

In some embodiments of the disclosed methods, the composition administered to the patient may include as a substrate ketoprofen. The method further may include detecting one or more metabolites selected from beta-estradio-3-glucuronide, trifluoperazine-N-glucuronide, 5-hydroxytryptophol-O-glucuronide, propofol-O-glucuronide, zidovudine-5'-glucuronide, and combinations thereof.

The disclosed methods may include determining a metabolic ratio based on one or more metabolites detected in saliva versus one or more unconverted substrates detected in saliva (e.g., METCYP/SUBCYP detected in saliva after having administered SUBCYP and having waiting for a period of time such as 0.5, 1.0, 1.5, 2.0, 2.5, 3.0, 3.5, 4.0, 4.5, 5.0, 5.5, 6.0, 7.0, 8.0, 9.0, 10.0, 11.0, 12.0, 24.0 hours or more). The disclosed methods may include determining a metabolic ratio for one or more of: (i) $MET_{CYP1A2}$ and unconverted $SUB_{CYP1A2}$ (e.g., caffeine versus paraxanthine); (ii) $MET_{CYP2C19}$ and unconverted $SUB_{CYP2}C19$ (e.g., omeprazole versus 5OH-omeprazole); (iii) $MET_{CYP2D6}$ and unconverted $SUB_{CYP2D6}$ (e.g., dextromethorphan versus dextrorphan); (iv) $MET_{CYP3A4}$ and unconverted $SUB_{CYP3A4}$ (e.g., 6I3-hydroxyeplerenone and/or 21-hydroxyeplerenone versus eplerenone); (v) $MET_{CYP2C9}$ and unconverted $SUB_{CYP2C9}$; (vi) $MET_{CYP2E1}$ and unconverted $SUB_{CYP2E1}$; and (vii) $MET_{CYP3A5}$ and unconverted $SUB_{CYP3A5}$.

Also disclosed herein are compositions suitable for use in the disclosed methods. The disclosed compositions typically comprise one or more substrates for one or more CYP isoforms (e.g., one or more substrates for one or more of CYP1A2, CYP2C9, CYP2C19, CYP2E1, CYP2D6, CYP3A4, and CYP3A5). In some embodiments, the compositions may comprise one or more of: (i) a substrate for CYP1A2 ($SUB_{CYP1A2}$), wherein CYP1A2 catalyzes conversion of $SUB_{1A2}$ to a metabolite ($MET_{CYP1A2}$); (ii) a substrate for CYP2C19 ($SUB_{CYP2C19}$), wherein CYP2C19 catalyzes conversion of $SUB_{2C19}$ to a metabolite ($MET_{CYP2C19}$); (iii) a substrate for CYP2D6 ($SUB_{CYP2D6}$), wherein $CYP_{2D6}$ catalyzes conversion of $SUB_{CYP2D6}$ to a metabolite ($MET_{CYP2D6}$); and (iv) a substrate for CYP3A4 ($SUB_{CYP3A4}$), wherein $CYP_{3A4}$ catalyzes conversion of $SUB_{CYP3A4}$ to a metabolite ($MET_{CYP3A4}$). Substrates for the disclosed compositions may include one or more "drugs" as known in the art and as provided above in the "Table of Exemplary Drugs."

In the disclosed compositions may comprise one or more tablet formulations of one or more substrates selected from $SUB_{CYP1A2}$, $SUB_{CYP2C19}$, $SUB_{CYP2D6}$, and $SUB_{CY3A4}$. In some embodiments, the composition includes multiple tablets, for example, one tablet each of $SUB_{CYP1A2}$, $SUB_{CYP2C19}$, $SUB_{CYP2D6}$, and $SUB_{CY3A4}$. In other embodiments, the composition administered to the patient may comprise a single tablet formulation, the single table formulation including each of substrates including one or more of $SUB_{CYP1A2}$, $SUB_{CYP2C19}$, $SUB_{CYP2D6}$, and $SUB_{CY3A4}$. Suitable tablet formulations may include immediate release tablet formulations, for example an immediate table release formulation for one or more of $SUB_{CYP1A2}$, $SUB_{CYP2C19}$, $SUB_{CYP2D6}$, and $SUB_{CY3A4}$. In some embodiments, the tablet formulations may include a non-substrate coating (e.g., an enteric coating).

The disclosed compositions typically include a substrate for one or more isoforms of CYP. In some embodiments, a substrate of the composition is a substrate for more than one isoform of CYP (e.g., a substrate for CYP1A2 may additionally be a substrate for another isoform of CYP such as any of CYP2C9, CYP2C19, CYP2E1, CYP2D6, CYP3A4, and CYP3A5). In other embodiments, a substrate of the composition is a substrate for one isoform of CYP and is not a substrate for another or any other isoform of CYP (e.g., a substrate for CYP3A4 may not be a substrate for another or any other of CYP1A2, CYP2C9, CYP2C19, CYP2E1, CYP2D6, and CYP3A5).

As such, the disclosed compositions may comprise one or more of $SUB_{CYP1A2}$, $SUB_{CYP2C19}$, $SUB_{CYP2D6}$, and $SUB_{CYP3A4}$. In some embodiments of the disclosed compositions, $SUB_{CYP1A2}$ may also be a substrate for other CYP isoforms or substrates for other enzymes. For example, $SUB_{CYP1A2}$ also may be a substrate for an enzyme selected from the group consisting of CYP2A6, NAT2, XO, and combinations thereof. In some embodiments, of the disclosed compositions, $SUB_{CYP2C19}$ may also be a substrate for other CYP isoforms or substrates for other enzymes. For example $SUB_{CYP2C19}$ may also be a substrate for CYP3A4. Suitable substrates for the disclosed composition may include, but are not limited to, one or more of: (i) $SUB_{CYP1A2}$ selected from caffeine and theophylline; (ii) $SUB_{CYP2C19}$ selected from omeprazole, esomeprazole, mephenytoin, clopidogrel, and phenytoin; (iii) $SUB_{CYP2D6}$ selected from dextromethorphan, desipramine, and metoprolol; and (iv) $SUB_{CYP3A4}$ selected from eplerenone, midazolam, simvastatin, alfentanil, dextrormethorphan, omeprazole, erythromycin, cortisol, midazolam, quindine, and triazolam. In particular, suitable substrates for the disclosed compositions may include one or more of caffeine, omeprazole, dextromethorphan, and eplerenone, and optionally a basic buffering agent, which may include but is not limited to sodium bicarbonate and/or calcium carbonate. Optionally, the disclosed mixtures may include a substrate for one or more of CYP2C9, CYP2E1, and CYP3A5.

Optionally, the disclosed compositions further may comprise a substrate for a non-CYP450 enzyme selected from an N-acetyl transferase (NAT), a methyl transferase, a UDP glucuronosyl transferase (UGT), a sulfo transferases, and an oxidative enzyme, or a combination thereof. Optionally, the compositions further comprises a substrate for an isoform of UDP glucuronosyl transferase (UGT) selected from the group consisting of UGT1A1, UGT1A4, UGT1A6, UGT1A9, and UGT2B7. Optionally, the disclosed compositions further may comprise ketoprofen.

The substrates utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, an immediate release form. In some embodiment, the substrates may be formulated in the same dosage form (e.g., all tablet form). In other embodiments, the substrates may be formulated in different dosage forms (e.g., some in tablet form others in powder form).

In some embodiments, the disclosed composition may include a buffer. For example, the composition may include a basic buffering agent, which may include but is not limited to sodium bicarbonate and/or calcium carbonate.

In some embodiments, the disclosed composition may have s a basic pH when the composition is dissolved in water. For example, the composition may have a pH greater than about 7.5, 8.0, 8.5, or 9.0 when dissolved in water.

The substrates utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The substrates utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

The substrates utilized in the methods disclosed herein may be formulated as a pharmaceutical composition for delivery via any suitable route. For example, the pharmaceutical composition may be administered via oral routes, sublingual routes, or buccal routes. Examples of pharmaceutical compositions for administration include capsules, syrups, concentrates, powders and granules. Suitable capsules may include hard gelatin capsules or softgels (aka soft gelatin capsules).

The substrates utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Also disclosed herein are kits. The disclosed kits may be utilized for testing metabolic activity in a patient and/or determining a phenotype of a patient. For example, the kits may be utilized for testing metabolic activity of one or more CYP450 isoforms and/or determining a phenotype of a patient in regarding to the activity of one or more CYP450 isoforms. The disclosed kits may include as a component any of the compositions and/or substrates disclosed herein. In some embodiments, the disclosed kits include one or more additional components selected from the group consisting of: (i) containers (e.g., salivettes) for collecting and transporting saliva samples; (ii) components and/or reagents for performing a UPLC-MS/MS assay; and/or (iii) components for generating a report of the results of the UPLC-MS/MS assay.

EXAMPLES

The following Examples are illustrative and are not intended to limit the scope of the claimed subject matter.

Example 1. CYP450 Phenotyping Using a Probe Mélange and a Saliva Sample

A. Materials and Methods

I. Cohort Characteristics

Healthy adult, primarily Caucasian college students and faculty aged 18-65 were enrolled in the study from February 2013 to April 2015. Exclusion criteria included allergy to caffeine, dextromethorphan, or omeprazole. Other exclusion criteria were pregnancy, possible pregnancy, or chronic illness.

II. Saliva Collection Protocol v1.

The patient is instructed as follows:

1. Do not drink or eat anything with caffeine or related products (ex. tea, coffee, chocolate, guarana extract) after 9 pm.

2. Drink a glass of water after waking. Wait 1 hour, then spit at least 0.5 ml of a saliva sample into a centrifuge tube (typically 500 mcL of liquid not including bubbles is required). Label this saliva sample "0". Place your initials on the tube, and place the tube in the freezer. Note: Do not try to express saliva (i.e., do not try to make more), just release what is already in your mouth.

3. Take 2 Robitussin® tablets (dextromethorphan 30 mg), 1 Prilosec OTC® (omeprazole 20 mg), and 1 caffeine tablet (caffeine 200 mg). Record the time in your lab notebook.

4. Drink a glass of water every couple hours.

5. Four, Six, and Eight hours after taking the pills, spit out at least 0.5 ml of a saliva sample into a centrifuge tube and label the tubes "4, 6, and 8" respectively. Initial the tubes and place the tubes in the freezer. Record the time.

III. Saliva Extraction a.k.a. Oral Fluid Extraction

Method A

1. Withdraw 500 mcL saliva and place into a new 1.5 mL centrifuge tube, also labeled with identifier and the sample number 0, 4, 6, or 8. Repeat with the other three saliva samples. Spike all four samples with 10 mcL internal standard solution (i.e., for effective quantitation in the final instrumental analysis), add 490 mcL of methanol, and mix by vortexing.

2. Freeze the samples in a −80° C. freezer (in the research lab in Heidelberg or Barth).

3. Remove the samples from the freezer once frozen (which typically takes ~60-90 minutes) and thaw.

4. Centrifuge the samples in the Eppendorf centrifuge at 13,100 RPM for 3 minutes.

5. Transfer 500 mcL of supernatant to a 3 kDa molecular weight cutoff centrifugal filter (Amicon Ultra 0.5 mL, or VWR 0.5 mL) nested in a new 1.5 mL centrifuge tube labeled with subject number and sample number, 0, 4, 6, or 8.

6. Centrifuge the tube and sieve at 13,100 RPM for 30 minutes.

7. Remove 350 mcL of supernatant (flow through) from the bottom of the centrifuge tube from step 6 and mix it with 150 mcL of deionized $H_2O$ in a HPLC vial labeled with your study number and 0, 4, 6, or 8 to identify the sample.

Method B

1. Freeze the samples in a −80° C. freezer to denature salivary proteins (See Francis et al., Arch. Oral. Biol. 45(7):601-606).

2. Remove the samples from the freezer once frozen (takes ~60-90 minutes) and thaw.

3. Centrifuge the samples in an Eppendorf centrifuge at 13,100 RPM for 5 minutes to precipitate mucous and denatured (from freezing) salivary protein.

4. Decant saliva supernate into a new 1.5 mL centrifuge tube. Withdraw 250 mcL saliva and place into another new 1.5 mL centrifuge tube. Also labeled with identifier and the sample number 0, 4, 6, or 8. Repeat with the other three saliva samples. Spike all four samples with 50 mcL internal standard solutions (for effective quantitation in the final instrumental analysis), add 200 mcL of methanol, and mix by vortexing.

5. Centrifuge the samples in the Eppendorf centrifuge at 13,100 RPM for 5 minutes to precipitate residual protein and lipid from saliva.

6. Transfer supernate to a 3 kDa molecular weight cutoff centrifugal filter (Amicon Ultra 0.5 mL, or VWR 0.5 mL) nested in a new 1.5 mL centrifuge tube labeled with subject number and sample number, 0, 4, 6, or 8.

7. Centrifuge the samples at 13,100 RPM for 30 minutes.

8. Remove supernate (flow through) from the bottom of the centrifuge tube from step 7 and place in an 300 mcl HPLC vial insert.

IV. UHPLC—MS/MS Method

Two UHPLC MS/MS methods were developed for initial data collection (Method 1 and Method 2).

The UHPLC parameters for Method 1 are described in Table 1. The MS/MS instrument parameters for Method 1 are described in Table 2. Optimal voltage settings for each substrate and metabolite were determined via syringe pump direct infusion of each standard in 50% methanol/water solution. The optimized mass spectrometer parameters for Method 1 are listed in Table 3.

The UHPLC parameters for Method 2 are described in Table 4. The MS/MS instrument parameters for Method 2 are described in Table 5. The optimized mass spectrometer parameters for Method 2 are listed in Table 6.

Standard curves were created using multiple injections at each data point for external standards from 0.06 to 1000 ng/ml. Product quantification was performed using AB Sciex Multiquant software version 2.0.2.

TABLE 1

Method 1 UHPLC Parameters

| Instrument Parameters | | Gradient Parameters | |
|---|---|---|---|
| | | Time (min) | % Sol'n B |
| Instrument | Dionex RSLC 3000 UHPLC | | |
| Column | Acquity HSS T3 1.8 mcm (2.1 × 100 mm) | −2 | 20 |
| Precolumn | Acquity HSS T3 1.8 mcm Vanguard | 0 | 20 |
| Flow rate | 0.25 ml/min | 7 | 80 |
| Solution A | Water w 0.1% FA | 10.5 | 80 |
| Solution B | ACN/THF/FA 20/4/0.1% | 11 | 20 |
| Inj. volume | 10 mcl | 15 | End |
| Wash sol'n | 70% B/30% A | | |
| Software | DCMS Link v. 2.8.0 | | |

ACN—acetonitrile,
THF—tetrahydrofuran,
FA—formic acid,
Sol'n—solution,
Inj.—Injection

TABLE 2

Method 1 MS/MS Parameters

| Instrument Information | | Source Parameters | |
|---|---|---|---|
| Instrument | Sciex 4000 Qtrap | Curtain Gas | 20 PSI |
| Source | Turbo V | Collision Gas | Medium |
| Probe | ESI | Ion Spray Voltage | 4500 V |
| Software | Analyst v.1.5.1 | Source T | 550° C. |
| Scan time | 50 ms | Gas 1 | 45 PSI |
| Mode | Positive | Gas 2 | 60 PSI |

T—temperature,
ESI—electrospray ionization

TABLE 3

Method 1 Optimized Mass Spectrometer Parameters

| Parent Drug or Metabolite | Precursor (m/z) | Product (m/z) | DP (eV) | CE (eV) | CXP (eV) |
|---|---|---|---|---|---|
| Paraxanthine | 181 | 124 | 30 | 30 | 12 |
| Caffeine | 195 | 138 | 80 | 27 | 11 |
| Dextrorphan | 258 | 133 | 100 | 50 | 8 |
| Methoxymorphinan | 258 | 213 | 100 | 35 | 17 |
| Dextromethorphan | 272 | 215 | 45 | 33 | 15 |
| Omeprazole | 346.4 | 198 | 45 | 15 | 10 |
| 5-Hydroxy Omeprazole | 362.4 | 214.2 | 55 | 17 | 15 |
| Diazepam | 285 | 193 | 90 | 45 | 13 |

EP = 10

TABLE 4

Method 2 UHPLC Parameters

| Instrument Parameters | | Gradient Parameters | |
|---|---|---|---|
| | | Time (min) | % Sol'n B |
| Instrument | Dionex RSLC 3000 UHPLC | | |
| Column | Acquity HSS T3 1.8 mcm (2.1 × 100 mm) | 0 | 10 |
| Precolumn | Acquity HSS T3 1.8 mcm Vanguard | 0.2 | 90 |
| Flow rate | 0.3 ml/min | 3.2 | 90 |
| Solution A | Water w 0.1% FA | 3.7 | 10 |

TABLE 4-continued

Method 2 UHPLC Parameters

| Instrument Parameters | | Gradient Parameters | |
|---|---|---|---|
| | | Time (min) | % Sol'n B |
| Instrument | Dionex RSLC 3000 UHPLC | | |
| Solution B | Methanol w 0.1% FA | 4.2 | 10 |
| Software | DCMS Link v. 2.8.0 | 5 | End |
| Inj. volume | 10 mcl | | |
| Wash sol'n | 70% B/30% A | | |
| Software | DCMS Link v. 2.8.0 | | |

ACN—acetonitrile,
FA—formic acid,
Sol'n—solution,
Inj.—Injection

TABLE 5

Method 2 MS/MS Parameters

| Instrument Information | | Source Parameters | |
|---|---|---|---|
| Instrument | Sciex 4000 Qtrap | Curtain Gas | 20 PSI |
| Source | Turbo V | Collision Gas | High |
| Probe | ESI | Ion Spray Voltage | 4500 V |
| Software | Analyst v.1.5.1 | Source T | 550° C. |
| Scan time | 50 ms | Gas 1 | 45 PSI |
| Mode | Positive | Gas 2 | 60 PSI |

T—temperature,
ESI—electrospray ionization

TABLE 6

Method 2 Optimized MS/MS Parameters

| Parent Drug or Metabolite | Precursor (m/z) | Product (m/z) | DP (eV) | CE (eV) | CXP (eV) |
|---|---|---|---|---|---|
| Paraxanthine | 181 | 124 | 30 | 30 | 12 |
| Caffeine | 195 | 138 | 80 | 27 | 11 |
| Dextrorphan | 258 | 133 | 100 | 50 | 8 |
| Methoxymorphinan | 258 | 213 | 100 | 35 | 17 |
| Dextromethorphan | 272 | 215 | 45 | 33 | 15 |
| Omeprazole | 346.4 | 198 | 45 | 15 | 10 |
| 5-Hydroxy Omeprazole | 362.4 | 214.2 | 55 | 17 | 15 |
| Diazepam | 285 | 193 | 90 | 45 | 13 |

EP = 10

B. Results

Phenotyping results were generated for caffeine as a probe of CYP1A2, omeprazole as a probe for CYP2C19, and dextromethorphan as a probe for CYP2D6 in healthy adults.

I. Caffeine Probe of CYP1A2 Phenotype

Caffeine is commonly used as a probe in phenotyping studies and does not interact with the other probes used in our mélange. Studies differ in their reports of CYP1A2 phenotype as determined by caffeine. Different researchers describe the histogram as unimodal, bimodal, or trimodal. (See Zhou et al., Drug Metab. Rev. 41(2):89-295). In our cohort of primarily Caucasian subjects we observe a primarily unimodal distribution with outliers forming a small extreme mode. Our extreme mode corresponds to poor metabolizers and represents 7.8% of our subjects. This is in agreement with another study of Australian Caucasians which reported 5% poor metabolizers. (See Ilett et al., Clin. Pharmacol. Ther. 54(3):317-322).

II. Omeprazole Probe of CYP2C19 Phenotype

Omeprazole has been used as a phenotyping probe for CYP2C19 in several studies in urine and plasma but never saliva. Omeprazole is commonly used as a probe in phenotyping studies and does not interact with the other probes used in our mélange. Our saliva phenotyping results show a complex multimodal histogram consistent with other studies in other matrices. Frequencies of individuals within the different modes of the salivary CYP2C19 metabolic phenotype histogram corresponds very well with known frequencies of phenotypes reported based on known genetic polymorphisms. The literature reports ranges of metabolic phenotypes as percentages: Ultra-rapid (2±4), Rapid (18±17), Extensive (51±15), Intermediate (34±17), Poor (7±8) (McGraw 2014). Literature reported percentages show close agreement with our findings: Ultra-rapid (2.4), Rapid (9.6), Extensive (49.4), Intermediate (31.3), and Poor (7.2).

We experienced problems with quantification of omeprazole in some saliva samples due to very low concentrations of both omeprazole and 5OH-omeprazole. These problems have been overcome by creating an immediate release formulation with increased dosage of omeprazole and added buffer.

III. Dextromethorphan Probe of CYP2D6 Phenotype

Dextromethorphan is commonly used as a probe in phenotyping studies and does not interact with the other probes used in our mélange. The literature reported percentages of CYP2D6 metabolic phenotypes from a validation study based on genetic and phenotypic analysis were: Ultra-rapid (~1-2%), Extensive (~77-92%), Intermediate (~2-11%), and Poor (~5-10%). (See Gaedigk et al., Clin Pharma Ther 83(2): 234-242; Crews et al., Clin Pharma Ther 95(4): 376-382; and Fang et al. Pharmacogenomics J 14(6): 564-572). Literature reported percentages show close agreement with our findings: Ultra-rapid (2.3%), Extensive (83.9%), Intermediate (9.2%), and Poor (4.6%).

DISCUSSION

The oral mélange of caffeine, dextromethorphan, and omeprazole is the first to simultaneously probe CYP1A2, CYP2D6, and CYP2C19 using saliva as a matrix. The results show good agreement with known rates of metabolic phenotypes in other primarily Caucasian cohorts.

Salivary caffeine/paraxanthine metabolic ratio is an accepted measure of caffeine metabolic phenotype. Phenotypic examination using a substrate probe is necessary because genetics only explain approximately 42% of CYP1A2 catalytic activity and the common polymorphisms effect enzyme induction rather than enzyme activity (Klein, Winter et al. 2010).

Omeprazole is an accepted probe of CYP2C19 activity in urine and plasma. However, the utility of omeprazole as a probe in saliva has not been previously reported. This is likely due to the low salivary concentrations of omeprazole and its metabolite 5-hydroxy omeprazole. However, we were able to develop a very sensitive assay which could simultaneously measure caffeine, dextromethorphan, omeprazole and their major metabolites in saliva.

An early paper by Hou et al. determined that saliva was an appropriate matrix for CYP2D6 phenotyping in a Chinese cohort. (See Hou et al., Clin. Pharmacol. Ther. 59(4):411-417). They described an antimode (MR=14) in healthy subjects determined 3 hours after a 50 mg immediate release (drug powder in capsule) marking the beginning of poor metabolizer MRs. In another study of patients with renal disease they used a lower 30 mg immediate release dose (drug powder in capsule) and the antimode at 3 hours was higher (MR=33). (See Hou et al., Clin Pharmacol Ther 59(4):411-417). Our antimode for dextromethorphan 6 hours after a 30 mg delayed release dose is MR=27.5. It is not surprising that the MR is similar amongst studies since Yeh et al. showed a stable MR in plasma whether an immediate release (Medicon® 15 mg) or extended release formulation (Detusiv® 60 mg) was given and the MR was maintained over several hours. (See Yeh et al., J. Biomed. Sci. 10(5):552-564). In a study by Hu et al., significant variability was found for repeated measures of dextromethorphan MRs from saliva samples taken 3 and 5 hours after a single 15 mg dose of Medicon while the 4 hour sample was borderline significant and the 6 hour sample was acceptable. (See Hu et al., J. Pharmacol. Exp. Ther. 285(3):955-960). These data provide external validation of our data.

Future work is aimed at expanding the study populations in which the probe mélange is used and expanding the probe set. Our preliminary studies have investigated CYP3A4 probes to add to the mélange for salivary analysis. Probe substrates were chosen based on safety considerations and previous reports of utility as CYP3A4 probes. Substrates we have tested include atorvastatin, cortisol, eplerenone, erythromycin, dextromethorphan, and omeprazole. Salivary concentrations represent free drug and metabolite concentrations. Therefore, metabolite production and diffusion ability must be high with low plasma protein binding for sufficient parent drug and metabolite to be present in saliva. Our preliminary results show erythromycin is the most promising candidate for a salivary CYP3A4 probe. Since genetics only explain a small fraction of CYP3A4 activity, the need for a rapid, inexpensive method to probe CYP3A4 activity is urgently needed.

REFERENCES

Crews, K. R., A. Gaedigk, H. M. Dunnenberger, J. S. Leeder, T. E. Klein, K. E. Caudle, C. E. Haidar, D. D. Shen, J. T. Callaghan, S. Sadhasivam, C. A. Prows, E. D. Kharasch, T. C. Skaar and C. P. I. Consortium (2014). "Clinical Pharmacogenetics Implementation Consortium guidelines for cytochrome P450 2D6 genotype and codeine therapy: 2014 update." Clin Pharmacol Ther 95(4): 376-382.

Crouch, D. J., Day, J., Baudys, Jakub, and Fatah, A. A., "Evaluation of Saliva/Oral Fluid as an Alternate Drug Testing Specimen," NIJ Report 605-03, Document No. 203569, February 2005.

Donzelli, M., Derungs, A., Serratore, M.-G., Noppen, C., Nezic, L., Krtihenbihl, S., and Haschke, M., "The Basel Cocktail for Simultaneous Phenotyping of Human Cytochrome P450 Isoforms in Plasma, Saliva and Dried Blood Spots, Clin Pharmacokinet (2014) 53:271-282.

Fang, H., X. Liu, J. Ramfrez, N. Choudhury, M. Kubo, H. K. Im, A. Konkashbaev, N. J. Cox, M. J. Ratain, Y. Nakamura and P. H. O'Donnell (2014). "Establishment of CYP2D6 reference samples by multiple validated genotyping platforms." Pharmacogenomics J 14(6): 564-572.

Gaedigk, A., S. D. Simon, R. E. Pearce, L. D. Bradford, M. J. Kennedy and J. S. Leeder (2008). "The CYP2D6 activity score: translating genotype information into a qualitative measure of phenotype." Clin Pharmacol Ther 83(2): 234-242.

Hou, Z. Y., C. P. Chen, W. C. Yang, M. D. Lai, E. T. Buchert, H. M. Chung, L. W. Pickle and R. L. Woosley (1996). "Determination of dextromethorphan metabolic phenotype by salivary analysis with a reference to genotype in Chinese patients receiving renal hemodialysis." Clin Pharmacol Ther 59(4): 411-417.

Hou, Z. Y., L. W. Pickle, P. S. Meyer and R. L. Woosley (1991). "Salivary analysis for determination of dextromethorphan metabolic phenotype." Clin Pharmacol Ther 49(4): 410-419.

Hu, O. Y., H. S. Tang, H. Y. Lane, W. H. Chang and T. M. Hu (1998). "Novel single-point plasma or saliva dextromethorphan method for determining CYP2D6 activity." J Pharmacol Exp Ther 285(3): 955-960.

Ilett, K. F., W. M. Castleden, Y. K. Vandongen, M. C. Stacey, M. A. Butler and F. F. Kadlubar (1993). "Acetylation phenotype and cytochrome P450IA2 phenotype are unlikely to be associated with peripheral arterial disease." Clin Pharmacol Ther 54(3): 317-322.

Klein, K., S. Winter, M. Turpeinen, M. Schwab and U. M. Zanger (2010). "Pathway-Targeted Pharmacogenomics of CYP1A2 in Human Liver." Front Pharmacol 1: 129.

McGraw, J. (2014). Chapter 16—CYP450 and Ethnicity A2—Padmanabhan, Sandosh. Handbook of Pharmacogenomics and Stratified Medicine. San Diego, Academic Press: 323-340.

Yeh, G. C., P. L. Tao, H. O. Ho, Y. J. Lee, J. Y. Chen and M. T. Sheu (2003). "Analysis of pharmacokinetic parameters for assessment of dextromethorphan metabolic phenotypes." J Biomed Sci 10(5): 552-564.

Zhou, S. F., J. P. Liu and B. Chowbay (2009). "Polymorphism of human cytochrome P450 enzymes and its clinical impact." Drug Metab Rev 41(2): 89-295.

U.S. Pat. No. 8,315,815.

US Publication No. 20010036440 A1, published on Nov. 1, 2001.

US Publication No. 20030104453 A1, Jun. 5, 2003.

US Publication No. 20050032070 A1, Feb. 10, 2005.

EP Publication No. 0 921 396 A2, published on Jun. 9, 1999.

EP Publication No. 1 138 778 A2, published on Mar. 14, 2001.

PCT Publication No. WO 2001/092596, published on Aug. 4, 2011.

Example 2—Eplerenone Probe of CYP3A4 Phenotype

An extensive search was conducted for CYP3A4 probe substrates and their metabolites, which could be identified in saliva. Only safe probes that would have minimal to no side effects from a one-time dose were considered. Candidates were also selected based on optimal PK parameters such as low to no protein binding and significant lipophilicity, so that they could pass through biological membranes such as salivary glands, and be present in saliva. Although we could identify most probe parent drugs in saliva, metabolites were often too low to quantify and/or very short lived in saliva. However, unlike the other CYP3A4 probes tested, eplerenone and its primary metabolite, 6Beta-Hydroxy Eplerenone, were both found in sufficiently high concentrations in saliva.

UHPLC MS/MS methods were developed for initial data collection. The UHPLC parameters are described in Table 7. The MS/MS instrument parameters are described in Table 8. The optimized mass spectrometer parameters are listed in Table 9. The UHPLC parameters for Method 2 are described in Table 4. The MS/MS instrument parameters for Method 2 are described in Table 5. The optimized mass spectrometer parameters for Method 2 are listed in Table 6. Product quantification was performed using AB Sciex Multiquant software version 2.0.2.

TABLE 7

Method 3 UHPLC Parameters

| | Instrument Parameters | Gradient Parameters | |
|---|---|---|---|
| | | Time (min) | % Sol'n B |
| Instrument | Dionex RSLC 3000 UHPLC | −0.2 | 50 |
| Column | Acquity HSS T3 1.8 mcm (2.1 × 100 mm) | 0.3 | 50 |
| Precolumn | Acquity HSS T3 1.8 mcm Vanguard | 0.35 | 95 |
| Flow rate | 0.3 ml/min | 2.75 | 100 |
| Solution A | Water, 5% MeOH, w 0.05% AA | 2.8 | 0 |
| Solution B | 35% ACN/65% MeOH w 0.05% AA | 3.5 | End |
| Software | DCMS Link v. 2.8.0 | | |
| Inj. volume | 5 mcl | | |
| Wash sol'n | 50% B/50% A | | |
| Software | DCMS Link v. 2.8.0 | | |

ACN—acetonitrile,
AA—Acetic acid,
Sol'n—solution,
Inj.—Injection,
MeOH—methanol

TABLE 8

Method 3 MS/MS Parameters

| Instrument Information | | Source Parameters | |
|---|---|---|---|
| Instrument | Sciex 4000 Qtrap | Curtain Gas | 30 PSI |
| Source | Turbo V | Collision Gas | High |
| Probe | ESI or APCI* | Ion Spray Voltage | 5500 V |
| Software | Analyst v.1.5.1 | Source T | 400° C. |
| Scan time | 50 ms | Gas 1 | 80 PSI |
| Mode | Positive | Gas 2 | 60 PSI |

T—temperature,
ESI—electrospray ionization,
*APCI used for eplerenone and metabolite, ESI for all others

TABLE 9

Method 3 Optimized MS/MS Parameters

| Parent Drug or Metabolite | Precursor (m/z) | Product (m/z) | DP (eV) | CE (eV) | CXP (eV) |
|---|---|---|---|---|---|
| Paraxanthine | 181 | 124 | 30 | 30 | 12 |
| Caffeine | 195 | 138 | 80 | 27 | 11 |
| Dextrorphan | 258 | 133 | 100 | 50 | 8 |
| Methoxymorphinan | 258 | 213 | 100 | 35 | 17 |
| Dextromethorphan | 272 | 215 | 45 | 33 | 15 |
| Omeprazole | 346.4 | 198 | 45 | 15 | 10 |
| 5-Hydroxy Omeprazole | 362.4 | 214.2 | 55 | 17 | 15 |
| Eplerenone | 415 | 163 | 60 | 30 | 10 |
| 6Beta-Hydroxy Eplerenone | 131 | 211 | 60 | 20 | 10 |
| Diazepam | 285 | 193 | 90 | 45 | 13 |

EP = 10

Table 10. shows the salivary $\log_{10}$ molar metabolic ratios for eplerenone and its metabolite 6Beta-Hydroxy Eplerenone, which is formed via CYP3A4.

TABLE 10

$\log_{10}$ Eplerenone/6Beta-Hydroxy Eplerenone Metabolic Ratios

| Subject | Time = 0.5 hr | Time = 1 hr | Time = 2 hr | Time = 3 hr |
|---|---|---|---|---|
| 4 | 0.36 | 0.24 | 0.12 | 0.15 |
| 5 | 0.49 | 0.40 | 0.30 | 0.18 |
| 1 | 0.59 | 0.42 | 0.35 | 0.26 |
| 7 | 0.61 | 0.48 | 0.36 | 0.53 |
| 6 | NA | 0.52 | 0.49 | 0.69 |

As indicated in Table 10, the metabolic ratios are fairly stable over different time points. The 3 hour time point may be the best choice because the distribution phase will be over after 2 hours because eplerenone exhibits a $T_{max}$ of approximately 1.5 hours. Five healthy volunteers aged 22-44 years old were given 50 mg of commercially available generic eplerenone. As expected, the range of values is not very wide. Constitutive CYP3A4 variability is estimated at about 5-fold; however, illness, inhibition, and induction-related interactions can enhance variability [1,2] with estimates ranging 40-50-fold in different populations [3].

REFERENCES

[1] Wilkinson G R. Drug metabolism and variability among patients in drug response. N Engl J Med 2005; 352(21): 2211-21.
[2] Ingelman-Sundberg M. Human drug metabolising cytochrome P450 enzymes: properties and polymorphisms. Naunyn Schmiedebergs Arch Pharmacol 2004; 369(1):89-104.
[3] Galetin A, Brown C, Hallifax D, Ito K, Houston J B. Utility of recombinant enzyme kinetics in prediction of human clearance: impact of variability, CYP3A5, and CYP2C19 on CYP3A4 probe substrates. Drug Metab Dispos 2004; 32(12):1411-20.

Example 3—Optimized Formulations for Detection of Metabolites in Saliva

In our initial studies with over the counter formulations of caffeine, dextromethorphan, and omeprazole we identified several problems. Caffeine doses of 200 mg were very high for some individuals and they complained of nervousness and anxiety. Dextrorphan, the dextromethorphan metabolite, was sometimes found in very low concentrations in saliva of individuals dosed with over the counter formulations. In addition, 5-hydroxy omeprazole and omeprazole were also found in low concentrations in saliva of some individuals. To overcome these issues we began formulating immediate release tablets containing caffeine, dextromethorphan, and omeprazole with sodium or calcium bicarbonate. The bicarbonate salts were added to enhance stability of omeprazole as a dosage form as well as stability in the stomach. Without an enteric coating or base protection, omeprazole rapidly degrades in acidic gastric fluids. Table 11 lists several formulations that were tested for mélange prototypes. Formulation #4 was utilized for repeat metabolic ratio measurements.

TABLE 11

Formulations Tested for Parent and Metabolites in Saliva

| COMPONENT | #1 | #2 | #3 | #4 | #5 |
|---|---|---|---|---|---|
| Caffeine | 50 | 20 | 20 | 20 | 20 |
| Dextro-methorphan | 25 | 30 | 30 | 35 | 25 |
| Omeprazole | 20 | 25 | 25 | 30 | 30 |

TABLE 11-continued

Formulations Tested for Parent and Metabolites in Saliva

| COMPONENT | #1 | #2 | #3 | #4 | #5 |
|---|---|---|---|---|---|
| Flurbiprofen | | | 20 | | |
| Atorvastatin | | | | | 10 |
| Microcrystalline cellulose | 75 | 75 | 75 | 75 | 65 |
| Lactose monohydrate | 63.5 | 99 | | | |
| Calcium carbonate | 50 | 40 | | | |
| Sodium bicarbonate | | | 40 | 40 | |
| Xylitol | | | 72.9 | 82.9 | 82.75 |
| Croscarmellose sodium | 15 | | | | |
| Crospovidone | | 9 | 15 | 15 | 15 |
| Silicon dioxide | 0.3 | 0.6 | 0.6 | 0.6 | |
| Magnesium stearate | 1.5 | 1.5 | 1.5 | 1.5 | 1.25 |

Table 12. below shows that metabolic ratio measurements may be unstable during the absorption phase but become stable during the elimination phase.

TABLE 12

$Log_{10}$ Omeprazole/5-Hydroxy Omeprazole Metabolic Ratio Measurements after Repeat Doses of Formulation

| | | Metabolic Ratio Time points (h) | | | | |
|---|---|---|---|---|---|---|
| Subject | Tablet # | 0.5 | 1 | 2 | 3 | 4 |
| 1 | 1 | 3.5 | *3.1* | 2.0 | 1.6 | *1.1* |
| | 2 | 3.1 | *2.1* | *1.5* | 1.0 | *0.5* |
| 2 | 1 | 0.9 | *0.7* | 0.6 | 0.4 | 0.4 |
| | 2 | X | 1.2 | 0.5 | 0.4 | 1.2 |
| 3 | 1 | *1.2* | 0.7 | *0.3* | 0.7 | X |
| | 2 | *2.5* | *2.0* | 1.3 | 0.9 | 1.0 |
| 4 | 1 | 2.3 | 1.5 | 0.9 | 0.8 | 0.6 |
| | 2 | 1.4 | 1.1 | 0.8 | 0.6 | 0.6 |
| 5 | 1 | 2.3 | 1.3 | 1.1 | 0.6 | 0.4 |
| | 2 | 2.4 | 1.9 | 1.3 | 0.9 | 0.7 |
| 6 | 1 | *1.9* | 1.4 | 1.0 | 1.3 | 0.6 |
| | 2 | *1.4* | 1.2 | 1.2 | 1.3 | 0.9 |
| 7 | 1 | *1.8* | *1.0* | 0.4 | 0.05 | 0.03 |
| | 2 | *1.3* | 0.7 | 0.6 | 0.2 | 1.3 |

Bold italicized values were significantly different via two tailed paired t-test.
X—missing data due to inadequate sample.

All individuals showed maximal omeprazole concentrations in saliva at 0.5 or 1 hour. Time points after 4 hours were not reported as parent and metabolite concentrations approach the limit of detection after 4 hours. The data indicate that 3 hours (+/−0.5 hours) may be an optimal time point for reproducible metabolic ratio measurements of immediate release omeprazole.

A source of variability in omeprazole metabolic ratio measurements in saliva may be due to contamination of the mouth and saliva when the tablet is ingested. For example, contamination may occur due to residual powder from the tablet formulation contaminating the mouth and saliva. As such, formulations will be prepared with a film coating to impede powder contamination of the oral cavity while not disturbing rapid dissolution.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method comprising:
   (a) administering orally to a subject in need of an assessment of one or more of CYP1A2 activity, CYP2C19 activity, and CYP2D6 activity in the subject a composition comprising:
      (i) caffeine, wherein CYP1A2 catalyzes conversion of caffeine to paraxanthine;
      (ii) omeprazole, wherein CYP2C19 catalyzes conversion of omeprazole to a 5OH-omeprazole; and
      (iii) dextromethorphan, wherein CYP2D6 catalyzes conversion of dextromethorphan to a dextrorphan; and
   (b) quantifying in a saliva sample from the subject one or more of:
      (i) paraxanthine and unconverted caffeine;
      (ii) 5OH-omeprazole and unconverted omeprazole; and
      (iii) dextrorphan and unconverted dextromethorphan;
   (c) assessing one or more of the CYP1A2 activity, the CYP2C19 activity, and the CYP2D6 activity in the subject based on the quantified:
      (i) paraxanthine and unconverted caffeine;
      (ii) 5OH-omeprazole and unconverted omeprazole; and
      (iii) dextrorphan and unconverted dextromethorphan.

2. The method of claim 1, wherein the composition further comprises a substrate for CYP3A4 ($SUB_{CYP3A4}$), wherein CYP3A4 catalyzes conversion of $SUB_{CYP3A4}$ to a metabolite ($MET_{CYP3A4}$), wherein $SUB_{CYP3A4}$ is eplerenone and $MET_{CYP3A4}$ is 6β-hydroxyeplerenone and/or 21-hydroxyeplerenone.

3. The method of claim 1, further comprising administering ketoprofen to the subject, and the method further comprising quantifying in a biological sample from the subject metabolites selected from the group consisting of beta-estradio-3-glucuronide, trifluoperazine-N-glucuronide, 5-hydroxytryptophol-O-glucuronide, propofol-O-glucuronide, zidovudine-5'-glucuronide, and combinations thereof.

4. The method of claim 1, further comprising determining a metabolic ratio for one or more of: (i) paraxanthine and unconverted caffeine; (ii) 5OH-omeprazole and unconverted omeprazole; and (iii) dextrorphan and unconverted dextromethorphan, and after determining the metabolic ratio, the method further comprising administering a dose of a drug that is metabolized by one or more of CYP1A2, CYP2C19, and CYP2D6 other than caffeine, omeprazole, and dextromethorphan.

5. The method of claim 1, wherein the subject is experiencing hepatic failure.

6. The method of claim 1 comprising: quantifying in a saliva sample from the subject each of: (i) paraxanthine and unconverted caffeine; (ii) 5OH-omeprazole and unconverted omeprazole; and (iii) dextrorphan and unconverted dextromethorphan; and assessing each of the CYP1A2 activity, the CYP2C19 activity, and the CYP2D6 activity in the subject based on the quantified: (i) paraxanthine and unconverted caffeine; (ii) 5OH-omeprazole and unconverted omeprazole; and (iii) dextrorphan and unconverted dextromethorphan.

7. A method comprising:
(a) administering orally to a subject in need of an assessment of one or more of CYP1A2 activity, CYP2C19 activity, and CYP2D6 activity in the subject:
  (i) a first composition comprising caffeine, wherein CYP1A2 catalyzes conversion of caffeine to paraxanthine;
  (ii) a second composition comprising omeprazole, wherein CYP2C19 catalyzes conversion of omeprazole to 5OH-omeprazole; and
  (iii) a third composition comprising dextromethorphan, wherein CYP2D6 catalyzes conversion of dextromethorphan to dextrorphan; and
(b) quantifying in a saliva sample from the subject one or more of:
  (i) paraxanthine and unconverted caffeine;
  (ii) 5OH-omeprazole and unconverted omeprazole; and
  (iii) dextrorphan and unconverted dextromethorphan;
(c) assessing one or more of the CYP1A2 activity, the CYP2C19 activity, and the CYP2D6 activity in the subject based on the quantified:
  (i) paraxanthine and unconverted caffeine;
  (ii) 5OH-omeprazole and unconverted omeprazole; and
  (iii) dextrorphan and unconverted dextromethorphan.

8. The method of claim 7, further comprising administering a fourth composition comprising a substrate for CYP3A4 ($SUB_{CYP3A4}$), wherein CYP3A4 catalyzes conversion of $SUB_{CYP3A4}$ to a metabolite ($MET_{CYP3A4}$), wherein $SUB_{CYP3A4}$ is eplerenone and $MET_{CYP3A4}$ is 6β-hydroxyeplerenone and/or 21-hydroxyeplerenone.

9. The method of claim 7, further comprising administering ketoprofen to the subject, and the method further comprising quantifying in a biological sample from the subject metabolites selected from the group consisting of beta-estradio-3-glucuronide, trifluoperazine-N-glucuronide, 5-hydroxytryptophol-O-glucuronide, propofol-O-glucuronide, zidovudine-5'-glucuronide, and combinations thereof.

10. The method of claim 7, further comprising determining a metabolic ratio for one or more of: (i) paraxanthine and unconverted caffeine; (ii) 5OH-omeprazole and unconverted omeprazole; and (iii) dextrorphan and unconverted dextromethorphan, and after determining the metabolic ratio, the method further comprising administering a dose of a drug that is metabolized by one or more of CYP1A2, CYP2C19, and CYP2D6 other than caffeine, omeprazole, and dextromethorphan.

11. The method of claim 7, wherein the subject is experiencing hepatic failure.

12. The method of claim 7 comprising: quantifying in a saliva sample from the subject each of: (i) paraxanthine and unconverted caffeine; (ii) 5OH-omeprazole and unconverted omeprazole; and (iii) dextrorphan and unconverted dextromethorphan; and assessing each of the CYP1A2 activity, the CYP2C19 activity, and the CYP2D6 activity in the subject based on the quantified: (i) paraxanthine and unconverted caffeine; (ii) 5OH-omeprazole and unconverted omeprazole; and (iii) dextrorphan and unconverted dextromethorphan.

13. A method comprising:
(a) administering orally to a subject in need of an assessment of one or more of CYP1A2 activity, CYP2C19 activity, and CYP2D6 activity in the subject one or more compositions comprising:
  (i) caffeine, wherein CYP1A2 catalyzes conversion of caffeine to paraxanthine;
  (ii) omeprazole, wherein CYP2C19 catalyzes conversion of omeprazole to 5OH-omeprazole; and
  (iii) dextromethorphan, wherein CYP2D6 catalyzes conversion of dextromethorphan to dextrorphan; and
(b) quantifying in a saliva sample from the subject one or more of:
  (i) paraxanthine and unconverted caffeine;
  (ii) 5OH-omeprazole and unconverted omeprazole; and
  (iii) dextrorphan and unconverted dextromethorphan;
(c) assessing one or more of the CYP1A2 activity, the CYP2C19 activity, and the CYP2D6 activity in the subject based on the quantified:
  (i) paraxanthine and unconverted caffeine;
  (ii) 5OH-omeprazole and unconverted omeprazole; and
  (iii) dextrorphan and unconverted dextromethorphan.

14. The method of claim 13, wherein the one or more compositions further comprise a substrate for CYP3A4 ($SUB_{CYP3A4}$), wherein CYP3A4 catalyzes conversion of $SUB_{CYP3A4}$ to a metabolite ($MET_{CYP3A4}$), wherein $SUB_{CYP3A4}$ is eplerenone and $MET_{CYP3A4}$ is 6β-hydroxyeplerenone and/or 21-hydroxyeplerenone.

15. The method of claim 13, further comprising administering ketoprofen to the subject, and the method further comprising quantifying in a biological sample from the subject metabolites selected from the group consisting of beta-estradio-3-glucuronide, trifluoperazine-N-glucuronide, 5-hydroxytryptophol-O-glucuronide, propofol-O-glucuronide, zidovudine-5'-glucuronide, and combinations thereof.

16. The method of claim 13, further comprising determining a metabolic ratio for one or more of: (i) paraxanthine and unconverted caffeine; (ii) 5OH-omeprazole and unconverted omeprazole; and (iii) dextrorphan and unconverted dextromethorphan, and after determining the metabolic ratio, the method further comprising administering a dose of a drug that is metabolized by one or more of CYP1A2, CYP2C19, and CYP2D6 other than caffeine, omeprazole, and dextromethorphan.

17. The method of claim 13, wherein the subject is experiencing hepatic failure.

18. The method of claim 13 comprising: quantifying in a saliva sample from the subject each of: (i) paraxanthine and unconverted caffeine; (ii) 5OH-omeprazole and unconverted omeprazole; and (iii) dextrorphan and unconverted dextromethorphan; and assessing each of the CYP1A2 activity, the CYP2C19 activity, and the CYP2D6 activity in the subject based on the quantified: (i) paraxanthine and unconverted caffeine; (ii) 5OH-omeprazole and unconverted omeprazole; and (iii) dextrorphan and unconverted dextromethorphan.

* * * * *

UNITED STATES PATENT AND TRADEMARK OFFICE
CERTIFICATE OF CORRECTION

PATENT NO. : 10,927,398 B2
APPLICATION NO. : 15/779788
DATED : February 23, 2021
INVENTOR(S) : Joseph McGraw et al.

It is certified that error appears in the above-identified patent and that said Letters Patent is hereby corrected as shown below:

In the Specification

Column 9/10, Table of Exemplary Drugs for Assessing Metabolism by CYP2C19, DRUG Methylphenobarbital, "31-67" should be --11-67--.

Column 9/10, Table of Exemplary Drugs for Assessing Metabolism by CYP2D6, DRUG Tramadol, "5.6-5-7" should be --5.6-6.7--.

Column 9/10, Table of Exemplary Drugs for Assessing Metabolism by CYP2D6, DRUG Haloperidol, "92.5%" should be --88.4-92.5%--.

Column 11/12, Table of Exemplary Drugs for Assessing Metabolism by CYP2D6, "Dextromethophan" should be --Dextromethorphan--.

Column 11/12, Table of Exemplary Drugs for Assessing Metabolism by CYP3A4, "Alfazosin" should be --Alfuzosin--.

Column 11/12, Table of Exemplary Drugs for Assessing Metabolism by CYP3A4, "Almortriptan" should be --Almotriptan--.

Column 11/12, Table of Exemplary Drugs for Assessing Metabolism by CYP3A4, "Basentan" should be --Bosentan--.

Column 13/14, Table of Exemplary Drugs for Assessing Metabolism by CYP3A4, "Efavir enz" should be --Efavirenz--.

Column 25, Line 48, "Krthihenbihl" should be --Krähenbühl--.

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*

Column 25, Line 52, "Ramfrez" should be --Ramírez--.

Column 27, Table 9, Line 52, "131" should be --431--.